United States Patent
Bijanto et al.

(10) Patent No.: US 7,842,828 B2
(45) Date of Patent: Nov. 30, 2010

(54) METHOD FOR SEPARATING OUT AND RECOVERING DIALKYLTIN DIALKOXIDE

(75) Inventors: Budianto Bijanto, Tokyo (JP); Nobuhisa Miyake, Tokyo (JP)

(73) Assignee: Asahi Kasei Chemicals Corporation, Tokyo (JP)

(*) Notice: Subject to any disclaimer, the term of this patent is extended or adjusted under 35 U.S.C. 154(b) by 269 days.

(21) Appl. No.: 12/223,984

(22) PCT Filed: Feb. 22, 2007

(86) PCT No.: PCT/JP2007/053254
§ 371 (c)(1), (2), (4) Date: Aug. 14, 2008

(87) PCT Pub. No.: WO2007/097388
PCT Pub. Date: Aug. 30, 2007

(65) Prior Publication Data
US 2010/0160662 A1    Jun. 24, 2010

(51) Int. Cl.
C07F 7/22       (2006.01)
C07C 69/96    (2006.01)

(52) U.S. Cl. .................................. 556/89; 558/260

(58) Field of Classification Search ............ 556/89; 558/260
See application file for complete search history.

(56) References Cited

U.S. PATENT DOCUMENTS

| | | | |
|---|---|---|---|
| 5,545,600 A | 8/1996 | Knudsen et al. | |
| 2005/0080274 A1 | 4/2005 | Miyake et al. | 549/228 |
| 2005/0240045 A1 | 10/2005 | Miyake et al. | |

FOREIGN PATENT DOCUMENTS

| CA | 2 566 880 A1 | 11/2005 |
|---|---|---|
| EP | 1 460 056 A1 | 9/2004 |
| EP | 1 535 896 A1 | 6/2005 |
| EP | 1760085 | 3/2007 |
| JP | 2002-371084 | 12/2002 |

(Continued)

OTHER PUBLICATIONS

Davies et al. "Organotin chemistry. Part XI. The preparation of organotin alkoxides" Journal of Chemical Society (C), 23: 3972-3976 (1971).

(Continued)

*Primary Examiner*—Porfirio Nazario Gonzalez
(74) *Attorney, Agent, or Firm*—Morgan Lewis & Bockius LLP

(57) ABSTRACT

For an alkyltin alkoxide catalyst composition used in carbonate production, there is a problem that the alkyltin alkoxide catalyst composition is thermally decomposed by being heated in the production process, changing into an undistillable alkyltin alkoxide catalyst composition containing a high boiling deactivated component and an active component. The present invention provides a method for separating out and recovering the active component from the alkyltin alkoxide catalyst composition as a useful dialkyltin dialkoxide. According to the present invention, there is disclosed a method in which such an undistillable alkyltin alkoxide catalyst composition containing a high boiling deactivated component and an active component is reacted with an alcohol and/or a carbonate, so as to obtain a reaction liquid containing a product originating from the active component, and then the reaction liquid is subjected to distillation, so as to separate out and recover a dialkyltin dialkoxide from the product originating from the active component.

20 Claims, 3 Drawing Sheets

FOREIGN PATENT DOCUMENTS

| | | |
|---|---|---|
| JP | 2005-298433 | 10/2005 |
| JP | 2006-159090 | 6/2006 |
| JP | 2006-176411 | 7/2006 |
| JP | 2006-176412 | 7/2006 |
| WO | WO2004/014840 | 2/2004 |
| WO | WO 2004/014840 | 2/2004 |
| WO | WO 2005/111049 | 11/2005 |

OTHER PUBLICATIONS

Journal of the Chemical Society of Japan—Industrial Chemistry, 72(7): 1543-1549 (1969).

Choi et al. "Reaction of Dialkyltin Methoxide with Carbon Dioxide Relevant to the Mechanism of Catalytic Carbonate Synthesis" Journal of American Chemical Society, 121: 3793-3794 (1999).

Ballivet-Tkatchenko et al. "The role of distannoxanes in the synthesis of dimethyl carbonate from carbon dioxide" Applied Catalysis A: General, 255(1): 93-99 (2003).

Danielle Ballivet-Tkatchenko et al., Reactivity of di*tert*-butyldimethoxystannane with carbon dioxide and methanol: X-ray structure of the resulting complex, *Journal of Organometallic Chemistry*, 619 (2006), pp. 1498-1504.

METHOD FOR SEPARATING OUT AND RECOVERING DIALKYLTIN DIALKOXIDE

CROSS-REFERENCE TO RELATED APPLICATIONS

The present application is a U.S. National Phase Application of International Application PCT/JP2007/053254 (filed Feb. 22, 2007) which claims the benefit of Japanese Patent Application No. 2006-046596 (filed Feb. 23, 2006), both of which are hereby incorporated by reference in their entirety.

TECHNICAL FIELD

The present invention relates to separating out and recovering a dialkyltin dialkoxide from an alkyltin alkoxide catalyst composition used as a catalyst in ester or carbonate production.

BACKGROUND ART

A dialkyltin dialkoxide is very useful as a catalyst such as a carbonate synthesis catalyst, a transesterification reaction catalyst, a silicone polymer or urethane curing catalyst.

As a conventional process for producing a dialkyltin dialkoxide, there is known a method in which a dialkyltin oxide and an alcohol are subjected to a dehydration reaction, and a low boiling component containing water produced is removed from the reaction liquid (see, for example, Patent Document 1: U.S. Pat. No. 5,545,600, Patent Document 2: WO 2005/111049, Patent Document 3: Japanese Patent Application Laid-open No. 2005-298433, Non-Patent Document 1: Journal of Chemical Society, 23 (1971), 3972, Non-Patent Document 2: Journal of the Chemical Society of Japan—Industrial Chemistry, 72, 7 (1969), 1543).

This method using the dialkyltin oxide is presumed to involve an equilibrium reaction accompanied by dehydration as shown in following formula (6):

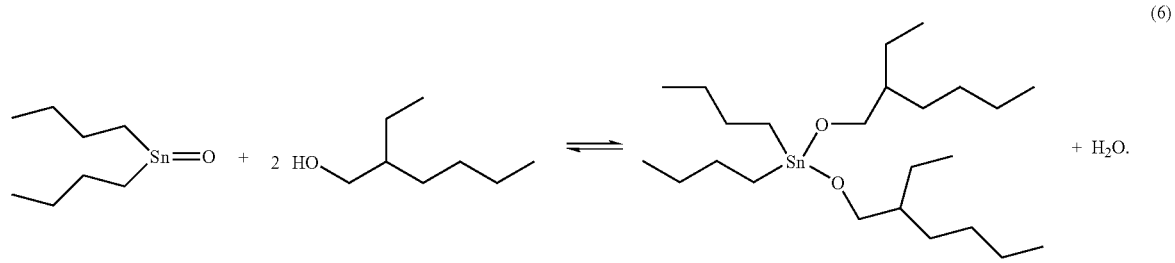

(6)

The above equilibrium is biased overwhelmingly toward the reactant system side, and furthermore the reaction is presumed to include successive dehydration reactions going via a tetraalkyltindistannoxane as shown in formulae (7) and (8) below. To obtain the dialkyltin dialkoxide with a high yield, production is carried out while withdrawing water out of the system from out of the dehydration reaction products, but this is an energetically unfavorable reaction, and hence the dialkyltin dialkoxide is obtained through prolonged reaction at a high temperature (e.g. 180° C.). The following dehydration reaction is carried out, and excess alcohol is removed from the reaction liquid, whereby a reaction liquid containing the dialkyltin dialkoxide is obtained.

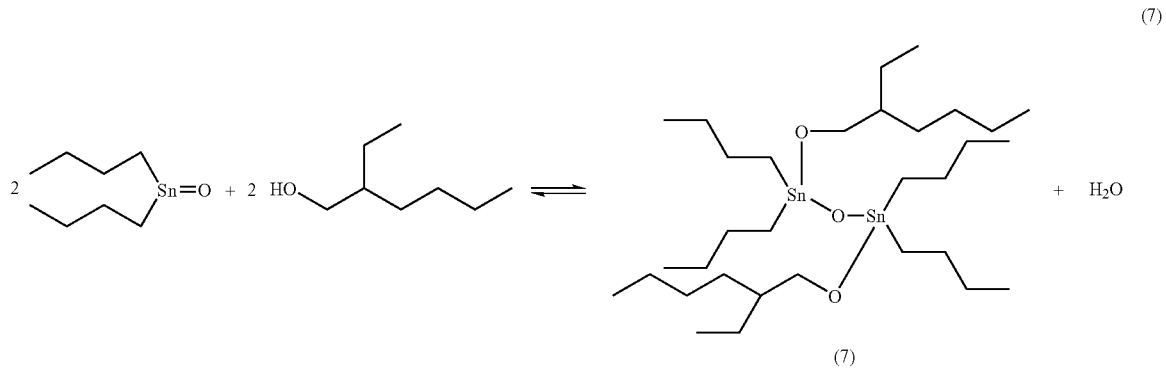

(7)

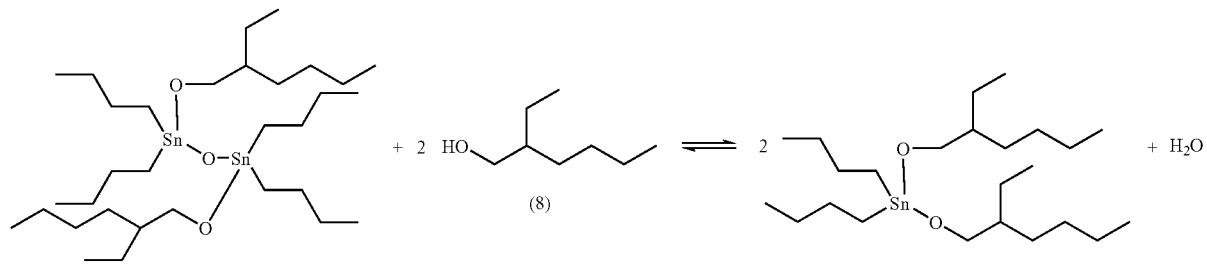

(8)

On the other hand, it is known that at such a high temperature, a dialkyltin compound is readily thermally decomposed into a trialkyltin compound (see, for example, Non-Patent Document 2: Journal of the Chemical Society of Japan—Industrial Chemistry, 72, 7 (1969), 1543). It is not clear by what reaction the trialkyltin compound is produced, but if it is assumed, for example, that the trialkyltin compound is produced through intramolecular alkyl group rearrangement, then it is presumed that the trialkyltin compound is produced by a disproportionation reaction as shown in following formula (9):

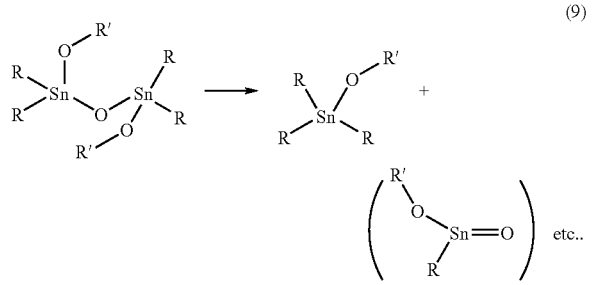

(9)

A dialkyltin dialkoxide obtained by a production process using the reaction described above is used, for example, for producing a carbonate through reaction with carbon dioxide (see, for example, Patent Document 2: WO 2005/111049). Thermally decomposed matter is produced in the dialkyltin dialkoxide production process as described above, but moreover it is presumed that in addition to this thermally decomposed matter is also produced in steps in which the dialkyltin compound is heated (e.g. the carbonate production step and a carbonate/dialkyltin compound separation step). Furthermore, it is known that such thermally decomposed matter contains the trialkyltin compound and a high-boiling-point tin component of unidentifiable structure, and that the trialkyltin compound exhibits hardly any activity in the carbonate synthesis using carbon dioxide (see, for example, Non-Patent Document 3: Journal of American Chemical Society, 121 (1999), 3793). In the present invention, the high-boiling-point tin component of unidentifiable structure in the thermally decomposed matter is referred to as a "high boiling deactivated component". Herein, "high-boiling-point" or "high boiling" means a boiling point at normal pressure higher than 250° C.

The above thermally decomposed matter is a deactivated component that does not exhibit reaction activity in the carbonate synthesis, and moreover, may cause a reduction in the reaction yield or contaminate the product, and hence must be separated out from the dialkyltin compound that is the active component (hereinafter, this component having two tin-carbon bonds on each tin atom constituting an alkyltin alkoxide is often referred to as the "active component").

The present inventors have previously disclosed an invention relating to production of a high-purity dialkyltin alkoxide (see, for example, Patent Document 3: Japanese Patent Application Laid-open No. 2005-298433). In this document, there is disclosed a process for producing a dialkyltin alkoxide not containing a harmful trialkyltin compound. As a result of their studies, the present inventors have ascertained that such a trialkyltin compound has a low boiling point among alkyltin alkoxide compounds, and hence a high-purity dialkyltin alkoxide can be obtained by removing the trialkyltin compound through distillation. On the other hand, a problem has remained that, of thermally decomposed matter, a high-boiling-point tin component of unidentifiable structure (the above "high boiling deactivated component") still remains mixed in with the active component.

Moreover, the present inventors have also disclosed an invention relating to production of a carbonate using an alkyltin alkoxide compound containing thermally decomposed matter (see, for example, Patent Document 4: WO 2004/014840). In this document, there is described a method in which, of the thermally decomposed matter, a trialkyltin compound component is separated out by distillation, so as to be prevented from accumulating in the reaction system.

However, for the thermally decomposed matter that is a counterpart to the trialkyltin compound, although a method has been described in which this thermally decomposed matter is precipitated out as solid utilizing the difference in melting point or solubility to the active component, and then separated out from the active component by filtration, so as to be prevented from accumulating in the reaction system, there have been cases in which the active component recovery yield decreases.

Patent Document 1: U.S. Pat. No. 5,545,600

Patent Document 2: WO 2005/111049

Patent Document 3: Japanese Patent Application Laid-open No. 2005-298433

Patent Document 4: WO 2004/014840

Non-Patent Document 1: Journal of Chemical Society, 23 (1971), 3972

Non-Patent Document 2: Journal of the Chemical Society of Japan—Industrial Chemistry, 72, 7 (1969), 1543

Non-Patent Document 3: Journal of American Chemical Society, 121 (1999), 3793

Non-Patent Document 4: Applied Catalysis A: General, 255 (2003), 93

DISCLOSURE OF INVENTION

Problems to be Solved by the Invention

The present inventors have carried out assiduous studies into the cause of the recovery yield decreasing, and as a result have obtained the following findings. Specifically, it is known that an active component tetraalkyldialkoxydistannoxane readily adopts a ladder structure as shown in the following formula (see, for example, Non-Patent Document 4: Applied Catalysis A: General, 255 (2003), 93). It has become clear that there is a problem that disproportionation under high temperature proceeds not only by the previously presumed formula (9), but also between two molecules forming a ladder structure as shown in following formula (10), and as a result some of the thermally decomposed matter (i.e. some of the above high-boiling-point tin component of unidentifiable structure) forms a compound in which the active component and the deactivated component are covalently bonded together, and hence in the above method using solidification, the active component covalently bonded to the deactivated component is removed together with the deactivated component so that the recovery yield is reduced, and the bonded deactivated component is recovered together with the active component, and hence still accumulates in the system. Other than separation by filtration or the like, separation by distillation can also be envisaged as an efficient separation recovery method, but neither the bonded deactivated component nor the deactivated component shown in formula (9) can be separated out from the active component by distillation (accordingly, in the present specification, of the product produced through thermal decomposition of the dialkyltin compound presumed to follow formula (9) and/or formula (10), the high-boiling-point tin component of unidentifiable structure other than the trialkyltin compound will be referred to as the "high boiling deactivated component").

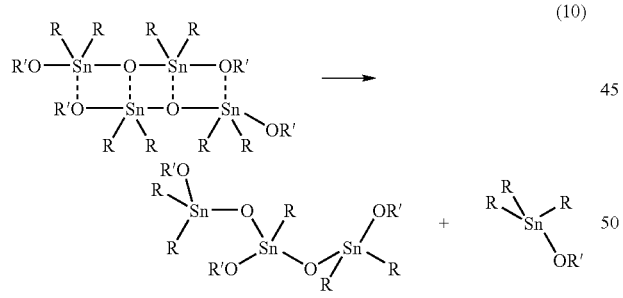

(10)

Moreover, the active component dialkyltin compound is expensive, and hence the recovery yield for the separation method is considered to be important. There have thus been needs for a separation method that enables the high boiling deactivated component and the active component, which cannot be separated from one another by distillation as described above, to be separated with a high active component recovery yield.

It is an object of the present invention to provide a separation recovery method for efficiently separating out and recovering an active component from an undistillable alkyltin alkoxide catalyst composition containing a high boiling deactivated component and the active component.

In view of the above circumstances, the present inventors carried out assiduous studies into separating out and recovering a dialkyltin alkoxide from an alkyltin alkoxide catalyst composition, and as a result accomplished the present invention upon discovering that the above object can be attained by reacting an undistillable alkyltin alkoxide catalyst composition containing a high boiling deactivated component and an active component with an alcohol and/or a carbonate, and then subjecting the reaction liquid thus obtained to distillation, so as to separate out and recover a product originating from the active component as a dialkyltin dialkoxide. That is, the present invention provides:

[1] a method for separating out and recovering an active component, by converting the active component into a dialkyltin dialkoxide, from an undistillable alkyltin alkoxide catalyst composition for use in a carbonate production, which contains a high boiling deactivated component and the active component, the method comprising the steps of:

(1) reacting the alkyltin alkoxide catalyst composition with an alcohol and/or a carbonate, so as to obtain a reaction solution containing a product originating from the active component; and (2) subjecting the reaction solution obtained in step (1) to distillation, so as to separate out and recover the dialkyltin dialkoxide from the product originating from the active component,

[2] the separation recovery method according to item [1], wherein the active component is a component having two tin-carbon bonds on each tin atom constituting an alkyltin alkoxide,

[3] the separation recovery method according to item [1] or [2], wherein the high boiling deactivated component has a boiling point higher than 250° C. at normal pressure,

[4] the separation recovery method according to any one of items [1] to [3], wherein the alkyltin alkoxide catalyst composition is not capable of being separated by distillation into the high boiling deactivated component and the active component at not more than 250° C. at normal pressure,

[5] the separation recovery method according to any one of items [1] to [4], wherein the active component is a tetraalkyldialkoxydistannoxane,

[6] the separation recovery method according to item [5], wherein the tetraalkyldialkoxydistannoxane is an alkyltin compound represented by following formula (1):

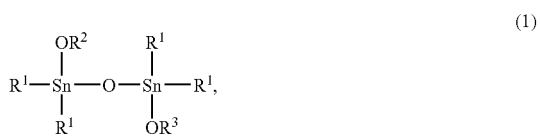

(1)

wherein $R^1$ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted or substituted aryl group having from 6 to 20 carbon atoms containing an alkyl selected from the group consisting of straight chain or branched alkyls having from 1 to 14 carbon atoms and cycloalkyls having from 5 to 14 carbon atoms; and each of $R^2$ and $R^3$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms,

[7] the separation recovery method according to any one of items [1] to [6], wherein the high boiling deactivated component is an alkyltin compound containing tin atoms that in $^{119}$Sn-NMR analysis exhibit chemical shifts in a range of from −220 to −610 ppm based on tetramethyltin,

[8] the separation recovery method according to item [1], wherein the alcohol is represented by following formula (2):

$$R^4\text{—OH} \qquad (2)$$

wherein $R^4$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms,

[9] the separation recovery method according to item [1], wherein the carbonate is represented by following formula (3):

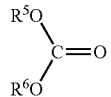

(3)

wherein each of $R^5$ and $R^6$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms,

[10] the separation recovery method according to item [1], wherein the dialkyltin dialkoxide is represented by following formula (4):

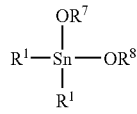

(4)

wherein $R^1$ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted or substituted aryl group having from 6 to 20 carbon atoms containing an alkyl selected from the group consisting of straight chain or branched alkyls having from 1 to 14 carbon atoms and cycloalkyls having from 5 to 14 carbon atoms; and each of $R^7$ and $R^6$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms; and each of $R^7$ and $R^8$ corresponds to an alkoxy group of the active component, $R^4$ in the alcohol, or $R^5$ or $R^6$ in the carbonate, wherein at least one of $R^7$ and $R^8$ corresponds to $R^4$, $R^5$ or $R^6$,

[11] the separation recovery method according to item [1], wherein the alkyltin alkoxide catalyst composition contains a dialkyltin oxide represented by following formula (5):

(5)

wherein $R^1$ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted substituted aryl group having from 6 to 20 carbon atoms containing an alkyl selected from the group consisting of straight chain or branched alkyls having from 1 to 14 carbon atoms and cycloalkyls having from 5 to 14 carbon atoms,

[12] the separation recovery method to item [6], wherein each alkyl group of the tetraalkyldialkoxydistannoxane is an n-butyl group or an n-octyl group,

[13] the separation recovery method according to item [8], wherein the alcohol is an alcohol selected from aliphatic alkyl alcohols having from 4 to 8 carbon atoms,

[14] the separation recovery method according to item [9], wherein the carbonate is a carbonate in which at least one of $R^5$ and $R^6$ is selected from aliphatic alkyl groups having from 4 to 8 carbon atoms,

[15] the separation recovery method according to item [11], wherein the dialkyltin oxide is a dialkyltin oxide selected from di-n-butyl-tin oxide and di-n-octyl-tin oxide,

[16] the separation recovery method according to item [1], wherein in step (1), a ratio of a total number of mols of the alcohol and/or the carbonate to the number of mols of tin atoms contained in the active component is in a range of from 2 to 100,

[17] the separation recovery method according to item [1], wherein in step (1), a reaction temperature is in a range of from 60 to 180° C.,

[18] the separation recovery method according to item [1], wherein the reaction of step (1) is carried out in a reactor of a type selected from the group consisting of a stirring tank reactor, a multi-stage stirring tank reactor, a packed column, a distillation column, a multi-stage distillation column, a continuous multi-stage distillation column, a reactor having a support therein, and a forced circulation reactor,

[19] the separation recovery method according to item [1], wherein in step (2), the separation by distillation is carried out in a distillation apparatus of a type selected from the group consisting of a multi-stage distillation column, a continuous multi-stage distillation column, a packed column, and a thin film evaporator,

[20] a process for producing a carbonate using a dialkyltin dialkoxide separated out and recovered using the method according to any one of items 1 to 19.

ADVANTAGEOUS EFFECTS OF THE INVENTION

According to the present invention, a dialkyltin dialkoxide which is a useful component can be efficiently separated out and recovered from the undistillable alkyltin alkoxide catalyst composition containing a high boiling deactivated component and an active component, and hence the present invention is highly useful industrially.

Figure 1:
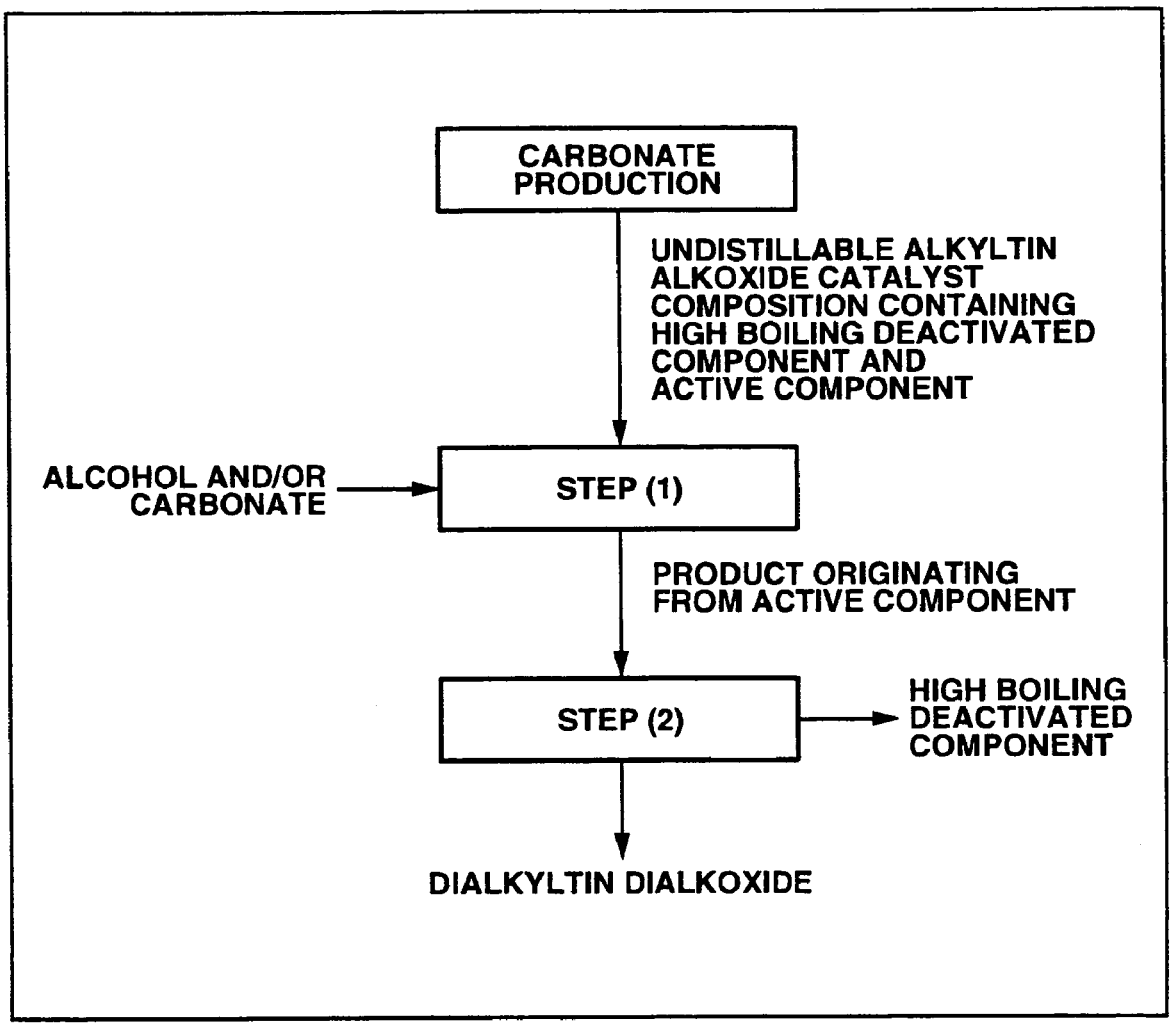
FIG. 1 illustrates a conceptual diagram showing a method for separating out and recovering a dialkyltin dialkoxide in the present invention.

DESCRIPTION OF REFERENCE NUMERALS 101, 107: distillation column; 102, 201: column reactor; 103, 106 thin film evaporator; 104: autoclave; 105: carbon dioxide removal tank; 111, 112, 117: reboiler; 121, 123, 126, 127: condenser; 211: lower portion of reactor; 221: upper portion of reactor; 1, 9, 21, 22: supply line; 2, 4, 5, 6, 7, 8, 10, 11, 12, 13, 14 transfer line; 3, 15, 23: recovery line; 16: withdrawal line; 17: feed line; 24: low boiling component recovery line.

BEST MODE FOR CARRYING OUT THE INVENTION

An embodiment of the present invention will now be described in detail. The following embodiment is merely illustrative for explaining the present invention, the present invention not being intended to be limited to only this embodiment. So long as the gist of the present invention is not deviated from, various modifications are possible.

In the present invention, an undistillable alkyltin alkoxide catalyst composition containing a high boiling deactivated component and an active component is reacted with an alcohol and/or a carbonate, and the reaction liquid thus obtained is subjected to distillation, so as to separate out and recover a dialkyltin dialkoxide from a product originating from the active component.

As described earlier, an alkyltin alkoxide catalyst composition used in a carbonate production is thermally decomposed through heating, forming thermally decomposed matter that does not exhibit activity in the carbonate production. The reaction mechanism of the thermal decomposition is not clear, but the thermal decomposition is presumed to occur through a disproportionation reaction as shown in following formula (9):

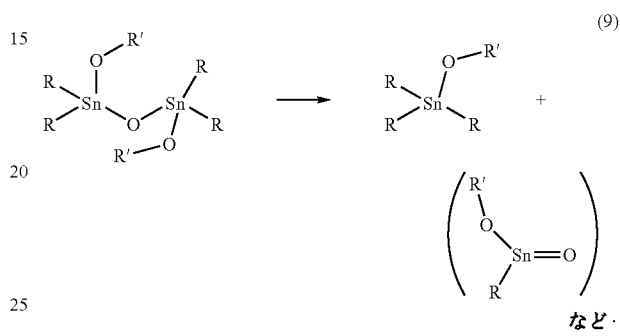

As shown in the above formula, upon an active component having two tin-carbon bonds on each tin atom undergoing thermal decomposition, the active component changes into thermally decomposed matter containing a trialkyltin compound and a high-boiling-point tin component of unidentifiable structure. Of the thermally decomposed matter, the trialkyltin compound (e.g. a trialkyltin alkoxide) has a relatively low boiling point among the components in the alkyltin alkoxide catalyst composition, and can thus be separated out from the active component by distillation. On the other hand, of the thermally decomposed matter, the high-boiling-point tin component of unidentifiable structure can be precipitated out as solid utilizing the difference in melting point or solubility to the active component, and then separated out (either partially or completely) from the active component by filtration, but it has been found that the active component recovery yield may be low. The present inventors carried out assiduous studies, and as a result conjectured that, because the active component tetraalkyldialkoxydistannoxane forms a dimer structure, and readily adopts a ladder structure as shown in following formula (10), the thermal decomposition results in not only the previously assumed formula (9) but also a compound in which the active component and part of the thermally decomposed matter are covalently bonded together as shown in following formula (10):

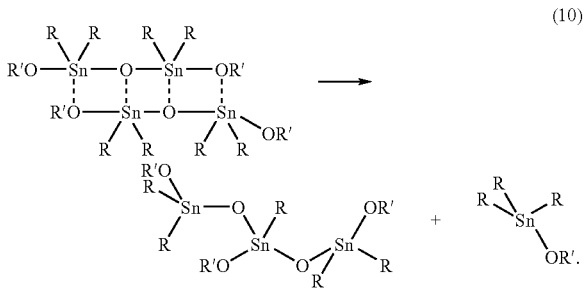

As a result, it is thought that in the above method using solidification, it is probably the case that the active component bonded to part of the thermally decomposed matter is removed together with the thermally decomposed matter, and hence the recovery rate is reduced, and conversely thermally decomposed matter is recovered together with the active component, and hence the separation cannot be carried out efficiently. As a separation method other than filtration, one can envisage separation by distillation, but under a degree of vacuum (e.g. a pressure of not less than 0.1 kPa) and a temperature of not more than 250° C. which is a temperature range easy to use industrially, it has not been possible to carry out separation from the alkyltin alkoxide catalyst composition containing the high boiling deactivated component and the active component. This is presumed to be because the high boiling deactivated component has a boiling point higher than 250° C. (at normal pressure), and moreover many tetraalkyldialkoxydistannoxanes (i.e. some active components) also having a boiling point higher than 250° C. (at normal pressure), and furthermore, in the case that the active component bonds to part of the thermally decomposed matter as conjectured above, because the boiling point of the bonded matter is generally higher than 250° C. (at normal pressure), and moreover due to the bonding, separating out of only the active component is impossible. Separation by distillation has thus been impossible under temperature and reduced pressure conditions that are easy to use industrially.

The present inventors thus carried out further assiduous studies, and as a result accomplished the present invention upon discovering that if the undistillable alkyltin alkoxide catalyst composition containing the high boiling deactivated component and the active component as described above is reacted with an alcohol and/or a carbonate, so as to obtain a reaction liquid containing a product originating from the active component, and the reaction liquid is subjected to distillation, then, surprisingly, a dialkyltin dialkoxide can be separated out and recovered from the product originating from the active component. That is, the present inventors have discovered a method for separating out and recovering the active component as the dialkyltin dialkoxide from the undistillable alkyltin alkoxide catalyst composition containing the high boiling deactivated component and the active component, and as a result have succeeded in enabling the active component to be separated out and recovered efficiently.

First, the compounds used in the present invention will be described. The active component used in the present invention is a component having two tin-carbon bonds on each tin atom constituting an alkyltin alkoxide, for example, a compound represented by chemical formula (1), chemical formula (4), or chemical formula (5):

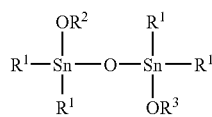

(1)

(wherein
R$^1$ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted or substituted aryl group having from 6 to 20 carbon atoms containing an alkyl selected from the group consisting of straight chain or branched alkyls having from 1 to 14 carbon atoms and cycloalkyls having from 5 to 14 carbon atoms; and each of R$^2$ and R$^3$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms; preferably, each of R$^2$ and R$^3$ is a straight chain or branched saturated aliphatic group having from 1 to 12 carbon atoms, more preferably a straight chain or branched alkyl group having from 1 to 12 carbon atoms.)

Examples of the tetraalkyldialkoxydistannoxane represented by formula (1) include
1,1,3,3-tetramethyl-1,3-dibutoxy-distannoxane (isomers),
1,1,3,3-tetramethyl-1,3-dipentyloxy-distannoxane (isomers),
1,1,3,3-tetramethyl-1,3-dihexyloxy-distannoxane (isomers),
1,1,3,3-tetrabutyl-1,3-dipropoxy-distannoxane (isomers),
1,1,3,3-tetrabutyl-1,3-dibutoxy-distannoxane (isomers),
1,1,3,3-tetraphenyl-1,3-dibutoxy-distannoxane (isomers),
1,1,3,3-tetraphenyl-1,3-dipentyloxy-distannoxane (isomers),
1,1,3,3-tetraphenyl-1,3-dihexyloxy-distannoxane (isomers),
1,1,3,3-tetrakis(trifluorobutyl)-1,3-dibutoxy-distannoxane (isomers),
1,1,3,3-tetrakis(trifluorobutyl)-1,3-dipentyloxy-distannoxane (isomers),
1,1,3,3-tetrakis(trifluorobutyl)-1,3-dihexyloxy-distannoxane (isomers),
1,1,3,3-tetrakis(pentafluorobutyl)-1,3-dibutoxy-distannoxane (isomers),
1,1,3,3-tetrakis(pentafluorobutyl)-1,3-dipentyloxy-distannoxane (isomers),
1,1,3,3-tetrakis(pentafluorobutyl)-1,3-dihexyloxy-distannoxane (isomers),
1,1,3,3-tetrakis(heptafluorobutyl)-1,3-dibutoxy-distannoxane (isomers),
1,1,3,3-tetrakis(heptafluorobutyl)-1,3-dipentyloxy-distannoxane (isomers),
1,1,3,3-tetrakis(heptafluorobutyl)-1,3-dihexyloxy-distannoxane (isomers),
1,1,3,3-tetrakis(nonafluorobutyl)-1,3-dibutoxy-distannoxane (isomers),
1,1,3,3-tetrakis(nonafluorobutyl)-1,3-dipentyloxy-distannoxane (isomers),
1,1,3,3-tetrakis(nonafluorobutyl)-1,3-dihexyloxy-distannoxane (isomers), and 1,1,3,3-tetraoctyl-1,3-dibutoxy-distannoxane (isomers). Preferable examples include tetraalkyldialkoxydistannoxanes in which R$^1$ is an alkyl group having from 1 to 12 carbon atoms. In the case that the number of carbon atoms is low, the product dialkyltin dialkoxide is prone to becoming solid, whereas in the case that the number of carbon atoms is high, the viscosity of the product may be high, so that the fluidity decreases. Particularly preferable examples thus include tetraalkyldialkoxydistannoxanes in which R$^1$ is an alkyl group having from 4 to 8 carbon atoms. Examples thereof include
tetra(n-butyl)-di(n-butoxy)-distannoxane,
tetra(n-butyl)-bis(2-methylpropyloxy)-distannoxane, tetra(n-butyl)-bis(3-methylbutyloxy)-distannoxane,
tetra(n-butyl)-bis(2-methylbutyloxy)-distannoxane,
tetra(n-butyl)-bis(2-ethylbutyloxy)-distannoxane,
tetra(n-octyl)-di(n-butoxy)-distannoxane,
tetra(n-octyl)-bis(2-methylpropyloxy)-distannoxane,
tetra(n-octyl)-bis(3-methylbutyloxy)-distannoxane,
tetra(n-octyl)-bis(2-methylbutyloxy)-distannoxane, and
tetra(n-octyl)-bis(2-ethylbutyloxy)-distannoxane. It is known that such a tetraalkyldialkoxydistannoxane represented by above formula (1) generally exists in the form of a multimer; in above formula (1), the tetraalkyldialkoxydistannoxane is shown with a monomer structure, but the tetraalkyldialkoxydistannoxane may have a multimer structure or comprise an aggregate.

The above tetraalkyldialkoxydistannoxane contained in the alkyltin alkoxide catalyst composition is readily hydrolyzed by water so as to change into a dialkyltin oxide represented by following formula (5), but the dialkyltin oxide can be changed back into the tetraalkyldialkoxydistannoxane through a dehydration reaction with an alcohol. The alkyltin alkoxide catalyst composition may thus contain the dialkyltin oxide represented by following formula (5):

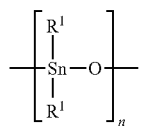

(5)

(wherein
$R^1$ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted or substituted aryl group having from 6 to 20 carbon atoms containing an alkyl selected from the group consisting of straight chain or branched alkyls having from 1 to 14 carbon atoms and cycloalkyls having from 5 to 14 carbon atoms.)

Examples of the dialkyltin oxide represented by above formula (5) include dimethyltin, oxide, diethyltin oxide, dipropyltin oxide (isomers), dibutyltin oxide (isomers), dipentyltin oxide (isomers), dihexyltin oxide (isomers), diheptyltin oxide (isomers), dioctyltin oxide (isomers), divinyltin oxide, diallyltin oxide, dicyclohexyltin oxide, dicyclooctyltin oxide, bis(trifluorobutyl)tin oxide, bis(pentafluorobutyl)tin oxide, bis(heptafluorobutyl)tin oxide, bis(nonafluorobutyl)tin oxide, diphenyltin oxide, dibenzyltin oxide, diphenethyltin oxide, and ditolyl tin oxide. Preferable examples include dialkyltin oxides in which $R^1$ is an alkyl group having from 1 to 12 carbon atoms. In the case that the number of carbon atoms is low, the product dialkyltin dialkoxide is prone to becoming solid, whereas in the case that the number of carbon atoms is high, the viscosity of the product may be high, so that the fluidity decreases. Particularly preferable examples thus include dialkyltin oxides in which $R^1$ is an alkyl group having from 4 to 8 carbon atoms, examples including di(n-butyl)tin oxide and di(n-octyl)tin oxide.

Next, the alkyltin alkoxide catalyst composition used in the present invention and the high boiling deactivated component will be described. The alkyltin alkoxide catalyst composition in the present invention can be obtained by reacting with carbon dioxide in a carbonate production, then separating off the carbonate by distillation, and then again subjecting the alkyltin alkoxide catalyst composition contained in the distillation residue to a dehydration reaction. The alkyltin alkoxide catalyst composition is heated in each step, and hence thermal decomposition occurs, so that a high boiling deactivated component is produced. The high boiling deactivated component in the present invention is thus a component obtained by thermal decomposition as the steps described below are repeated, being a high-boiling-point (boiling point higher than 250° C.) tin component of unidentifiable structure.

The carbonate production process in the present invention typically comprises the following steps:

Step (A): A step in which a starting material comprising a dialkyltin compound or a mixture obtained in step (C) below is subjected to a dehydration reaction with an alcohol as a reactant, thus obtaining a reaction liquid containing a dialkyltin dialkoxide derived from the dialkyltin compound.

Step (B): A step in which the reaction liquid obtained in step (A) is reacted with carbon dioxide, thus obtaining a reaction liquid containing a carbonate.

Step (C): A step in which the reaction liquid obtained in step (B) is separated by distillation into the carbonate, and a mixture containing the dialkyltin compound and thermally decomposed matter from the dialkyltin compound, and the mixture is returned into step (A) as starting material.

The temperature and pressure conditions differ between the respective steps. In step (A), the reaction is carried out, for example, at a temperature in a range of from 80 to 180° C. and a pressure in a range of from 20 to $1\times10^6$ Pa, so as to obtain the reaction liquid containing the dialkyltin dialkoxide. Next, in step (B), the reaction liquid obtained in step (A) and carbon dioxide are reacted together at, for example, a temperature in a range of from 80 to 180° C. and a pressure in a range of from 0.5 to 50 MPa-G, so as to obtain the reaction liquid containing the carbonate. Then, in step (C), the reaction liquid obtained in step (B) is subjected to distillation at, for example, a temperature in a range of from 100 to 250° C. and a pressure in a range of from 0.1 to $2\times10^5$ Pa, thus separating out the carbonate.

In this way, each of the steps is carried out at a respectively suitable temperature and pressure. In each of the steps, the temperature is higher than room temperature, the step being carried out in a heated state. On the other hand, for example, steps (A) and (C) are carried out at a relatively low pressure, whereas step (B) is carried out at a high pressure. Furthermore, in steps (B) and (C), carbon dioxide is added to the reaction system, and hence reaction that is different from the one in step (A) takes place. It is thus presumed that the thermally decomposed matter produced in the respective steps is due to different reactions, and hence the thermally decomposed matter is thought to be not only due to the dehydration reaction step as stated in the prior art, but rather is more complex.

It had been presumed that the thermally decomposed matter is produced through the disproportionation reaction shown in formula (9) below, but as described earlier, a tetraalkyldialkoxydistannoxane readily adopts a ladder structure, and hence it is thought that thermally decomposed matter is also produced through the reaction formula shown in formula (10) below. The thermally decomposed matter exhibits different chemical shifts to the active component in $^{119}$Sn- NMR analysis. Of the thermally decomposed matter, that presumed to be a trialkyltin compound (e.g. a trialkyltin alkoxide) exhibits a chemical shift of from 60 to 140 ppm based on tetramethyltin, whereas the high boiling deactivated component of unidentifiable structure contains a tin atoms exhibiting chemical shifts of from −220 to −610 ppm. The thermally decomposed matter may in some cases also contain a tetraalkyltin and/or tin oxide ($SnO_2$). However, the tetraalkyltin can be separated out by distillation or the like. Moreover, in the case that tin oxide is present, the tin oxide can be separated out together with the active component through the method of the present invention, and moreover the tin oxide is generally solid, and hence can be separated out using a publicly known method such as filtration.

The high boiling deactivated component in the present invention is a component produced through thermal decomposition of the active component as described above (e.g. formula (9) and/or formula (10). The present invention is preferably applied to a high boiling deactivated component produced from a tetraalkyldialkoxydistannoxane as above by thermal decomposition. The high boiling deactivated component produced from the tetraalkyldialkoxydistannoxane through the thermal decomposition has a boiling point higher than 250° C. (at normal pressure), and moreover cannot be separated out by distillation at not more than 250° C. from the corresponding tetraalkyldialkoxydistannoxane.

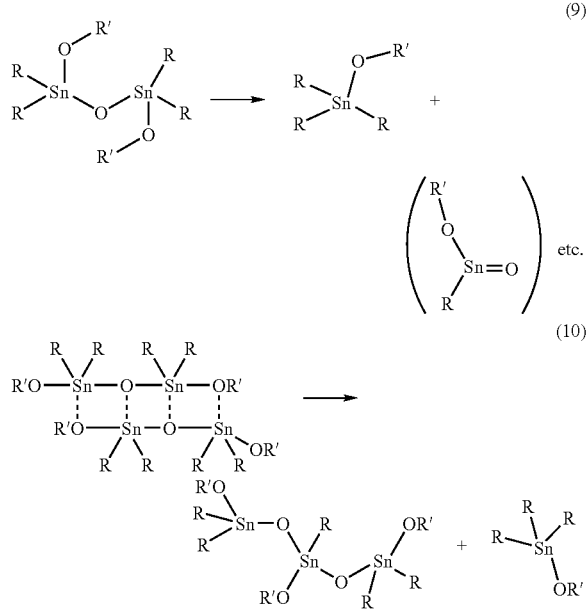

Examples of the trialkyltin alkoxide in formula (9) or (10) include trimethyl-methoxy-tin, trimethyl-ethoxy-tin, trimethyl-propoxy-tin (isomers), trimethyl-butoxy-tin (isomers), trimethyl-pentyloxy-tin (isomers), trimethyl-hexyloxy-tin (isomers), trimethyl-heptyloxy-tin (isomers), trimethyl-octyloxy-tin (isomers), trimethyl-nonyloxy-tin (isomers), trimethyl-decyloxy-tin (isomers), trimethyl-benzyloxy-tin, trimethyl-phenylethoxy-tin, butyl-dimethyl-methoxy-tin, butyl-dimethyl-ethoxy-tin, butyl-dimethyl-propoxy-tin (isomers), butyl-dimethyl-butoxy-tin (isomers), butyl-dimethyl-pentyloxy-tin (isomers), butyl-dimethyl-hexyloxy-tin (isomers), butyl-dimethyl-heptyloxy-tin (isomers), butyl-dimethyl-octyloxy-tin (isomers), butyl-dimethyl-nonyloxy-tin (isomers), butyl-dimethyl-decyloxy-tin (isomers), butyl-dimethyl-benzyloxy-tin, butyl-dimethyl-phenylethoxy-tin, dibutyl-methyl-methoxy-tin, dibutyl-methyl-ethoxy-tin, dibutyl-methyl-propoxy-tin (isomers), dibutyl-methyl-butoxy-tin (isomers), dibutyl-methyl-pentyloxy-tin (isomers), dibutyl-methyl-hexyloxy-tin (isomers), dibutyl-methyl-heptyloxy-tin (isomers), dibutyl-methyl-octyloxy-tin (isomers), dibutyl-methyl-nonyloxy-tin (isomers), dibutyl-methyl-decyloxy-tin (isomers), dibutyl-methyl-benzyloxy-tin, dibutyl-methyl-phenylethoxy-tin, butyl-diethyl-methoxy-tin, butyl-diethyl-ethoxy-tin, butyl-diethyl-propoxy-tin (isomers), butyl-diethyl-butoxy-tin (isomers), butyl-diethyl-pentyloxy-tin (isomers), butyl-diethyl-hexyloxy-tin (isomers), butyl-diethyl-heptyloxy-tin (isomers), butyl-diethyl-octyloxy-tin (isomers), butyl-diethyl-nonyloxy-tin (isomers), butyl-diethyl-decyloxy-tin (isomers), butyl-diethyl-benzyloxy-tin, butyl-diethyl-phenylethoxy-tin, dibutyl-ethyl-methoxy-tin, dibutyl-ethyl-ethoxy-tin, dibutyl-ethyl-propoxy-tin (isomers), dibutyl-ethyl-butoxy-tin (isomers), dibutyl-ethyl-pentyloxy-tin (isomers), dibutyl-ethyl-hexyloxy-tin (isomers), dibutyl-ethyl-heptyloxy-tin (isomers), dibutyl-ethyl-octyloxy-tin (isomers), dibutyl-ethyl-nonyloxy-tin (isomers), dibutyl-ethyl-decyloxy-tin (isomers), dibutyl-ethyl-benzyloxy-tin, dibutyl-ethyl-phenylethoxy-tin, butyl-dipropyl-methoxy-tin, butyl-dipropyl-ethoxy-tin, butyl-dipropyl-propoxy-tin (isomers), butyl-dipropyl-butoxy-tin (isomers), butyl-dipropyl-pentyloxy-tin (isomers), butyl-dipropyl-hexyloxy-tin (isomers), butyl-dipropyl-heptyloxy-tin (isomers), butyl-dipropyl-octyloxy-tin (isomers), butyl-dipropyl-nonyloxy-tin (isomers), butyl-dipropyl-decyloxy-tin (isomers), butyl-dipropyl-benzyloxy-tin, butyl-dipropyl-phenylethoxy-tin, dibutyl-propyl-methoxy-tin, dibutyl-propyl-ethoxy-tin, dibutyl-propyl-propoxy-tin (isomers), dibutyl-propyl-butoxy-tin (isomers), dibutyl-propyl-pentyloxy-tin (isomers), dibutyl-propyl-hexyloxy-tin (isomers), dibutyl-propyl-heptyloxy-tin (isomers), dibutyl-propyl-octyloxy-tin (isomers), dibutyl-propyl-nonyloxy-tin (isomers), dibutyl-propyl-decyloxy-tin (isomers), dibutyl-propyl-benzyloxy-tin, dibutyl-propyl-phenylethoxy-tin, tributyl-methoxy-tin, tributyl-ethoxy-tin, tributyl-propoxy-tin (isomers), tributyl-butoxy-tin (isomers), tributyl-benzyloxy-tin, tributyl-phenylethoxy-tin, triphenyl-methoxy-tin, triphenyl-ethoxy-tin, triphenyl-propoxy-tin (isomers), triphenyl-butoxy-tin (isomers), triphenyl-pentyloxy-tin (isomers), triphenyl-hexyloxy-tin (isomers), triphenyl-heptyloxy-tin (isomers), triphenyl-octyloxy-tin (isomers), triphenyl-nonyloxy-tin (isomers), triphenyl-decyloxy-tin (isomers), triphenyl-benzyloxy-tin, triphenyl-phenylethoxy-tin, methoxy-tris-(trifluorobutyl)-tin, ethoxy-tris-(trifluorobutyl)-tin, propoxy-tris-(trifluorobutyl)-tin (isomers), butoxy-tris-(trifluorobutyl)-tin (isomers), pentyloxy-tris-(trifluorobutyl)-tin (isomers), hexyloxy-tris-(trifluorobutyl)-tin (isomers), heptyloxy-tris-(trifluorobutyl)-tin (isomers), octyloxy-tris-(trifluorobutyl)-tin (isomers), nonyloxy-tris-(trifluorobutyl)-tin (isomers), decyloxy-tris-(trifluorobutyl)-tin (isomers), benzyloxy-tris-(trifluorobutyl)-tin, phenylethoxy-tris-(trifluorobutyl)-tin, methoxy-tris-(pentafluorobutyl)-tin, ethoxy-tris-(pentafluorobutyl)-tin, propoxy-tris-(pentafluorobutyl)-tin (isomers), butoxy-tris-(pentafluorobutyl)-tin (isomers), pentyloxy-tris-(pentafluorobutyl)-tin (isomers), hexyloxy-tris-(pentafluorobutyl)-tin (isomers), heptyloxy-tris-(pentafluorobutyl)-tin (isomers), octyloxy-tris-(pentafluorobutyl)-tin (isomers), nonyloxy-tris-(pentafluorobutyl)-tin (isomers), decyloxy-tris-(pentafluorobutyl)-tin (isomers), benzyloxy-tris-(pentafluorobutyl)-tin, phenylethoxy-tris-(pentafluorobutyl)-tin, methoxy-tris-(heptafluorobutyl)-tin, ethoxy-tris-(heptafluorobutyl)-tin, propoxy-tris-(heptafluorobutyl)-tin (isomers), butoxy-tris-(heptafluorobutyl)-tin (isomers), pentyloxy-tris-(heptafluorobutyl)-tin (isomers), hexyloxy-tris-(heptafluorobutyl)-tin (isomers), heptyloxy-tris-(heptafluorobutyl)-tin (isomers), octyloxy-tris-(heptafluorobutyl)-tin (isomers), nonyloxy-tris-(heptafluorobutyl)-tin (isomers), decyloxy-tris-(heptafluorobutyl)-tin (isomers), benzyloxy-tris-(heptafluorobutyl)-tin, phenylethoxy-tris-(heptafluorobutyl)-tin, methoxy-tris-(nonafluorobutyl)-tin, ethoxy-tris-(nonafluorobutyl)-tin, propoxy-tris-(nonafluorobutyl)-tin (isomers), butoxy-tris-(nonafluorobutyl)-tin (isomers), pentyloxy-tris-(nonafluorobutyl)-tin (isomers), hexyloxy-tris-(nonafluorobutyl)-tin (isomers), heptyloxy-tris-(nonafluorobutyl)-tin (isomers), octyloxy-tris-(nonafluorobutyl)-tin (isomers), nonyloxy-tris-(nonafluorobutyl)-tin (isomers), decyloxy-tris-(nonafluorobutyl)-tin (isomers), benzyloxy-tris-(nonafluorobutyl)-tin, and phenylethoxy-tris-(nonafluorobutyl)-tin.

Moreover, the details of the deactivated component that is a counterpart to the trialkyltin alkoxide produced through the disproportionation reaction shown in formula (9) are unclear, but examples include monoalkyltin alkoxide oxides. Examples thereof include monoalkyltin compounds such as methyl-methoxy-tin oxide, methyl-ethoxy-tin oxide, methyl-propoxy-tin oxide (isomers), methyl-butoxy-tin oxide (isomers), methyl-pentyloxy-tin oxide (isomers), methyl-hexyloxy-tin oxide (isomers), methyl-heptyloxy-tin oxide (isomers), methyl-octyloxy-tin oxide (isomers), methyl-nonyloxy-tin oxide (isomers), methyl-decyloxy-tin oxide (isomers), butyl-methoxy-tin oxide, butyl-ethoxy-tin oxide, butyl-propoxy-tin oxide (isomers), butyl-butoxy-tin oxide (isomers), butyl-benzyloxy-tin oxide, butyl-phenylethoxy-tin oxide, octyl-methoxy-tin oxide, octyl-ethoxy-tin oxide, octyl-propoxy-tin oxide (isomers), octyl-butoxy-tin oxide (isomers), octyl-benzyloxy-tin oxide, octyl-phenylethoxy-tin oxide, phenyl-methoxy-tin oxide, phenyl-ethoxy-tin oxide, phenyl-propoxy-tin oxide (isomers), phenyl-butoxy-tin oxide (isomers), phenyl-pentyloxy-tin oxide (isomers), phenyl-hexyloxy-tin oxide (isomers), phenyl-heptyloxy-tin oxide (isomers), phenyl-octyloxy-tin oxide (isomers), phenyl-nonyloxy-tin oxide (isomers), phenyl-decyloxy-tin oxide (isomers), phenyl-benzyloxy-tin oxide, phenyl-phenylethoxy-tin oxide, methoxy-(trifluoro-butyl)-tin oxide, ethoxy-(trifluoro-butyl)-tin oxide, propoxy-(trifluoro-butyl)-tin oxide (isomers), butoxy-(trifluoro-butyl)-tin oxide (isomers), pentyloxy-(trifluorobutyl)-tin oxide (isomers), hexyloxy-(trifluorobutyl)-tin oxide (isomers), heptyloxy-(trifluorobutyl)-tin oxide (isomers), octyloxy-(trifluorobutyl)-tin oxide (isomers), nonyloxy-(trifluorobutyl)-tin oxide (isomers), decyloxy-(trifluorobutyl)-tin oxide (isomers), benzyloxy-(trifluorobutyl)-tin oxide, phenylethoxy-(trifluorobutyl)-tin oxide, methoxy-(pentafluorobutyl)-tin oxide, ethoxy-(pentafluorobutyl)-tin oxide, propoxy-(pentafluorobutyl)-tin oxide (isomers), butoxy-(pentafluorobutyl)-tin oxide (isomers), pentyloxy-(pentafluorobutyl)-tin oxide (isomers), hexyloxy-(pentafluorobutyl)-tin oxide (isomers), heptyloxy-(pentafluorobutyl)-tin oxide (isomers), octyloxy-(pentafluorobutyl)-tin oxide (isomers), nonyloxy-(pentafluorobutyl)-tin oxide (isomers), decyloxy-(pentafluorobutyl)-tin oxide (isomers), benzyloxy-(pentafluorobutyl)-tin oxide, phenylethoxy-(pentafluorobutyl)-tin oxide, methoxy-(heptafluorobutyl)-tin oxide, ethoxy-(heptafluorobutyl)-tin oxide, propoxy-(heptafluorobutyl)-tin oxide (isomers), butoxy-(heptafluorobutyl)-tin oxide (isomers), pentyloxy-(heptafluorobutyl)-tin oxide (isomers), hexyloxy-(heptafluorobutyl)-tin oxide (isomers), heptyloxy-(heptafluorobutyl)-tin oxide (isomers), octyloxy-(heptafluorobutyl)-tin oxide (isomers), nonyloxy-(heptafluorobutyl)-tin oxide (isomers), decyloxy-(heptafluorobutyl)-tin oxide (isomers), benzyloxy-(heptafluorobutyl)-tin oxide, phenylethoxy-(heptafluorobutyl)-tin oxide, methoxy-(nonafluorobutyl)-tin oxide, ethoxy-(nonafluorobutyl)-tin oxide, propoxy-(nonafluorobutyl)-tin oxide (isomers), butoxy-(nonafluorobutyl)-tin oxide (isomers), pentyloxy-(nonafluorobutyl)-tin oxide (isomers), hexyloxy-(nonafluorobutyl)-tin oxide (isomers), heptyloxy-(nonafluorobutyl)-tin oxide (isomers), octyloxy-(nonafluorobutyl)-tin oxide (isomers), nonyloxy-(nonafluorobutyl)-tin oxide (isomers), decyloxy-(nonafluorobutyl)-tin oxide (isomers), benzyloxy-(nonafluorobutyl)-tin oxide, and phenylethoxy-(nonafluorobutyl)-tin oxide.

Next, the alcohol and carbonate used in the present invention will be described. First, as the alcohol, one having a chemical structure represented by following formula (2) can be used:

$$R^4-OH \quad (2)$$

(wherein $R^4$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms.).

Examples of the alcohol represented by above formula (2) include methanol, ethanol, propanol (isomers), butanol (isomers), pentanol (isomers), hexanol (isomers), heptanol (isomers), octanol (isomers), nonanol (isomers), decanol (isomers), cyclohexanol, cycloheptanol, cyclooctanol, phenylmethanol, and 2-phenyl-ethanol, preferable examples including butanol (isomers), pentanol (isomers), hexanol (isomers), heptanol (isomers), and octanol (isomers). Of these alcohols, n-butanol, 2-methyl-1-propanol, n-pentanol, 3-methyl-1-butanol, 2-methyl-1-butanol, n-hexanol, and 2-ethyl-1-butanol are particularly preferable.

Next, as the carbonate used in the present invention, one having a chemical structure represented by following formula (3) can be used:

(3)

(wherein:

each of $R^5$ and $R^6$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms.).

Examples of the carbonate represented by above formula (3) include dimethyl carbonate, diethyl carbonate, dipropyl carbonate (isomers), dibutyl carbonate (isomers), dipentyl carbonate (isomers), dihexyl carbonate (isomers), dioctyl carbonate (isomers), di(cyclopentyl)carbonate, di(cyclohexyl)carbonate, and dibenzyl carbonate. Particularly preferable carbonates are ones in which each of $R^5$ and $R^6$ in above chemical formula (4) is a straight chain or branched aliphatic group having from 4 to 8 carbon atoms, more preferably an aliphatic group having from 4 to 6 carbon atoms. Examples thereof include di-n-butyl carbonate, bis(2-methylpropyl) carbonate, di(n-pentyl)carbonate, bis(3-methylbutyl)carbonate, bis(2-methylbutyl)carbonate, di(n-hexyl)carbonate, and bis(2-ethylbutyl)carbonate.

The undistillable alkyltin alkoxide catalyst composition that contains the high boiling deactivated component and the active component as described above is reacted with the alcohol and/or carbonate, so as to obtain a reaction liquid containing a product originating from the active component, and then the reaction liquid is subjected to distillation, whereby a dialkyltin dialkoxide represented by following formula (4) can be separated out and recovered from the product originating from the active component:

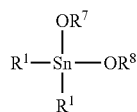

(4)

(wherein $R^1$ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted or substituted aryl group having from 6 to 20 carbon atoms containing an alkyl selected from the group consisting of straight chain or branched alkyls having from 1 to 14 carbon atoms and cycloalkyls having from 5 to 14 carbon atoms;

and each of $R^7$ and $R^8$ represents a straight chain or branched aliphatic group having from 1 to 12 carbon atoms, an alicyclic aliphatic group having from 5 to 12 carbon atoms, an substituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms; each of $R^7$ and $R^8$ corresponds to the alkoxy group of the active component, or $R^4$ in the alcohol, or $R^5$ or $R^6$ in the carbonate, wherein at least one of $R^7$ and $R^8$ corresponds to $R^4$, $R^5$ or $R^6$).

Examples of the dialkyltin dialkoxide represented by above formula (4) include alkylalkoxytin compounds such as dimethyl-dimethoxy-tin, dimethyl-diethoxy-tin, dimethyl-dipropoxy-tin (isomers), dimethyl-dibutoxy-tin (isomers), dimethyl-dipentyloxy-tin (isomers), dimethyl-dihexyloxy-tin (isomers), dimethyl-diheptyloxy-tin (isomers), dimethyl-dioctyloxy-tin (isomers), dimethyl-dinonyloxy-tin (isomers), dimethyl-didecyloxy-tin (isomers), butyl-dimethoxy-methyl-tin, butyl-diethoxy-methyl-tin, butyl-dipropoxy-methyl-tin (isomers), butyl-dibutoxy-methyl-tin (isomers), butyl-dipentyloxy-methyl-tin (isomers), butyl-dihexyl-methyl-tin (isomers), butyl-diheptyloxy-methyl-tin (isomers), butyl-dioctyloxy-methyl-tin (isomers), butyl-dimethoxy-ethyl-tin, butyl-diethoxy-ethyl-tin, butyl-dipropoxy-ethyl-tin (isomers), butyl-dibutoxy-ethyl-tin (isomers), butyl-dipentyloxy-ethyl-tin (isomers), butyl-dihexyl-ethyl-tin (isomers), butyl-diheptyloxy-ethyl-tin (isomers), butyl-dioctyloxy-ethyl-tin (isomers), butyl-dimethoxy-propyl-tin, butyl-diethoxy-propyl-tin, butyl-dipropoxy-propyl-tin (isomers), butyl-dibutoxy-propyl-tin (isomers), butyl-dipentyloxy-propyl-tin (isomers), butyl-dihexyloxy-propyl-tin (isomers), butyl-diheptyloxy-propyl-tin (isomers), butyl-dioctyloxy-propyl-tin (isomers), dibutyl-dimethoxy-tin, dibutyl-diethoxy-tin, dibutyl-dipropoxy-tin (isomers), dibutyl-dibutoxy-tin (isomers), dibutyl-bis(benzyloxy)-tin, dibutyl-bis(phenylethoxy)-tin, dioctyl-dimethoxy-tin, dioctyl-diethoxy-tin, dioctyl-dipropoxy-tin (isomers), dioctyl-dibutoxy-tin (isomers), dioctyl-bis(benzyloxy)-tin, dioctyl-bis(phenylethoxy)-tin, diphenyl-dimethoxy-tin, diphenyl-diethoxy-tin, diphenyl-dipropoxy-tin (isomers), diphenyl-dibutoxy-tin (isomers), diphenyl-di(pentyloxy)-tin (isomers), diphenyl-di(hexyloxy)-tin (isomers), diphenyl-di(heptyloxy)-tin (isomers), diphenyl-di(octyloxy)-tin (isomers), diphenyl-di(nonyloxy)-tin (isomers), diphenyl-di(decyloxy)-tin (isomers), diphenyl-bis(benzyloxy)-tin, diphenyl-bis(phenylethoxy)-tin, dimethoxy-bis-(trifluoro-butyl)-tin, diethoxy-bis-(trifluoro-butyl)-tin, dipropoxy-bis-(trifluorobutyl)-tin (isomers), dibutoxy-bis-(trifluoro-butyl)-tin (isomers), di(pentyloxy)-bis-(trifluorobutyl)-tin (isomers), di(hexyloxy)-bis-(trifluorobutyl)-tin (isomers), di(heptyloxy)-bis-(trifluorobutyl)-tin (isomers), di(octyloxy)-bis-(trifluorobutyl)-tin (isomers), di(nonyloxy)-bis-(trifluorobutyl)-tin (isomers), di(decyloxy)-bis-(trifluorobutyl)-tin (isomers), bis(benzyloxy)-bis-(trifluorobutyl)-tin, bis(phenylethoxy)-bis-(trifluorobutyl)-tin, dimethoxy-bis-(pentafluorobutyl)-tin, diethoxy-bis-(pentafluorobutyl)-tin, dipropoxy-bis-(pentafluorobutyl)-tin (isomers), dibutoxy-bis-(pentafluorobutyl)-tin (isomers), dipentyloxybis-(pentafluorobutyl)-tin (isomers), dihexyloxy-bis-(pentafluorobutyl)-tin (isomers), diheptyloxy-bis-(pentafluorobutyl)-tin (isomers), dioctyloxy-bis-(pentafluorobutyl)-tin (isomers), dinonyloxy-bis-(pentafluorobutyl)-tin (isomers), didecyloxy-bis-(pentafluorobutyl)-tin (isomers), bisbenzyloxy-bis-(pentafluorobutyl)-tin, bisphenylethoxy-bis-(pentafluorobutyl)-tin, dimethoxy-bis-(heptafluorobutyl)-tin, diethoxy-bis-(heptafluorobutyl)-tin, dipropoxy-bis-(heptafluorobutyl)-tin (isomers), dibutoxy-bis-(heptafluorobutyl)-tin (isomers), dipentyloxybis-(heptafluorobutyl)-tin (isomers), dihexyloxy-bis-(heptafluorobutyl)-tin (isomers), diheptyloxy-bis-(heptafluorobutyl)-tin (isomers), dioctyloxy-bis-(heptafluorobutyl)-tin (isomers), dinonyloxy-bis-(heptafluorobutyl)-tin (isomers), didecyloxy-bis-(heptafluorobutyl)-tin (isomers), bisbenzyloxy-bis-(heptafluorobutyl)-tin, bisphenylethoxy-bis-(heptafluorobutyl)-tin, dimethoxy-bis-(nonafluorobutyl)-tin, diethoxy-bis-(nonafluorobutyl)-tin, dipropoxy-bis-(nonafluorobutyl)-tin (isomers), dibutoxy-bis-(nonafluorobutyl)-tin (isomers), dipentyloxybis-(nonafluorobutyl)-tin (isomers), dihexyloxy-bis-(nonafluorobutyl)-tin (isomers), diheptyloxy-bis-(nonafluorobutyl)-tin (isomers), dioctyloxy-bis-(nonafluorobutyl)-tin (isomers), dinonyloxy-bis-(nonafluorobutyl)-tin (isomers), didecyloxy-bis-(nonafluorobutyl)-tin (isomers), bisbenzyloxy-bis-(nonafluorobutyl)-tin, and bisphenylethoxy-bis-(nonafluorobutyl)-tin. Particularly preferable examples include di(n-butyl)-di(n-butoxy)tin, di(n-butyl)-bis(3-methylbutyloxy)tin, di(n-butyl)-bis(2-methylbutyloxy)tin, di(n-butyl)-bis(2-ethylbutyloxy)tin, di(n-octyl)-di(n-butoxy)tin, di(n-octyl)-bis(3-methylbutyloxy)tin, di(n-octyl)-bis(2-methylbutyloxy)tin, and di(n-octyl)-bis(2-ethylbutyloxy)tin.

Several measurement examples in which such a dialkyltin dialkoxide represented by chemical formula (4), tetraalkyldialkoxydistannoxane represented by chemical formula (1), and trialkyltin alkoxide were analyzed by $^{119}$Sn-NMR are shown in Tables 1 and 2 below. In the $^{119}$Sn-NMR analysis, the chemical shift values for these tin compounds are prone to being affected by concentration, solvent and so on, and hence it is preferable to use the $^{119}$Sn-NMR in combination with $^{13}$C-NMR and $^{1}$H-NMR.

The peak width at half height is fairly, broad at 1 to 4 ppm for the $^{119}$Sn-NMR shift for a dialkyltin dialkoxide represented by chemical formula (4), and moreover the chemical shift value changes with concentration, moving toward higher magnetic field with increasing concentration. As a measurement example, analysis results for dibutyl-bis(2-ethylhexyloxy)-tin are shown in Table 1 below.

TABLE 1

TABLE 1: $^{119}$Sn-NMR CHEMICAL SHIFT FOR DIBUTYL-BIS(2-ETHYLHEXYLOXY)-TIN (SOLVENT: CDCl$_3$)

| CONCENTRATION [wt %] | $^{119}$Sn-NMR CHEMICAL SHIFT (ppm; BASED ON SnMe$_4$) |
|---|---|
| 3.4 | 2.7 |
| 11.2 | −6.6 |
| 20.5 | −19.1 |
| 48.3 | −64.2 |

On the other hand, for tetraalkyldialkoxydistannoxanes represented by chemical formula (1) and trialkyltin alkoxides, the $^{119}$Sn-NMR chemical shifts exhibit a sharp shape with a peak width at half height of 0.1 to 0.5 ppm, and the chemical shift values are not much affected by concentration, solvent and so on. As measurement examples, analysis results for several 1,1,3,3-tetrabutyl-1,3-bis(alkoxy)-distannoxanes and tributyl-(alkoxy)-tin compounds are shown in Table 2.

As shown above, for the dialkyltin dialkoxide, tetraalkyldialkoxydistannoxane, and trialkyltin alkoxide, identification by $^{119}$Sn-NMR is relatively easy. However, for the high boiling deactivated component of unidentifiable structure, upon analyzing by $^{119}$Sn-NMR, a plurality of chemical shifts are seen over a range of from −220 to −610 ppm. It is presumed that this phenomenon is due to the complex structure of high boiling deactivated component, and as the result the structure is extremely difficult to identify.

The thermally decomposed alkyltin alkoxide catalyst composition forms a mixture with a trialkyltin alkoxide and a high boiling deactivated component having a complex structure as described above, and moreover the reactivity and so on thereof is not clear; however, if the mixture is reacted with an alcohol and/or a carbonate so as to obtain a reaction liquid containing a product originating from the active component contained in the mixture, and then the reaction liquid is subjected to distillation, then surprisingly, a useful dialkyltin dialkoxide can be separated out and recovered from the product originating from the active component.

That is, in the present invention, as shown in FIG. 1, the undistillable alkyltin alkoxide catalyst composition obtained from carbonate production containing the high boiling deactivated component and the active component is reacted with an alcohol and/or a carbonate in step (1) so as to obtain a reaction liquid containing a product originating from the active component, and then the reaction liquid is subjected to distillation in step (2) so as to separate out and recover the dialkyltin dialkoxide from the product, originating from the active component.

Next, the reaction carried out in step (1) of the separation recovery method according to the present invention will be described. In the case that the undistillable alkyltin alkoxide catalyst composition containing the high boiling deactivated component and the active component is reacted with alcohol, it is presumed that dehydration takes place as follows.

TABLE 2

TABLE 2: $^{119}$Sn-NMR CHEMICAL SHIFT FOR 1,1,3,3-TETRABUTYL-1,3-DIALKOXY-DISTANNOXANES AND TRIBUTYL-(ALKOXY)-TIN COMPOUNDS (SOLVENT: CDCl$_3$)

| ALKOXY GROUP | $^{119}$Sn-NMR CHEMICAL SHIFTS FOR RESPECTIVE STRUCTURES (ppm; BASED ON SnMe$_4$) | | |
|---|---|---|---|
| | 1,1,3,3-TETRABUTYL-1,3-DIALKOXY-DISTANNOXANE | | TRIBUTYL-(ALKOXY)-TIN |
| METHOXY | −174.1 | −180.2 | 109.4 |
| BUTOXY | −177.5 | −187.1 | 101.0 |
| 2-METHYLPROPYLOXY | −174.5 | −184.5 | 100.7 |
| HEXYLOXY | −177.6 | −186.9 | 100.4 |
| 2-ETHYLBUTYLOXY | −172.5 | −184.5 | 100.8 |
| 2-ETHYLHEXYLOXY | −172.7 | −184.2 | 100.3 |

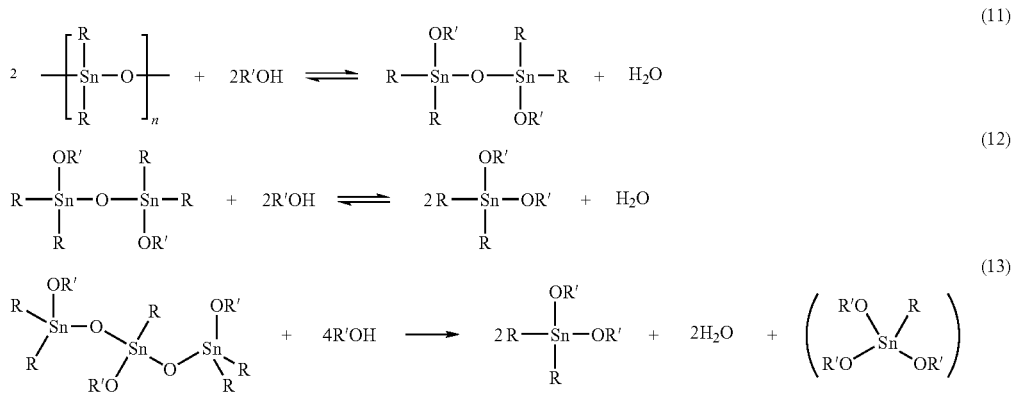

(11)
(12)
(13)

Moreover, in the case of using a carbonate, although the details of the reaction mechanism are not clear, it is presumed that reaction with release of carbon dioxide takes place as follows.

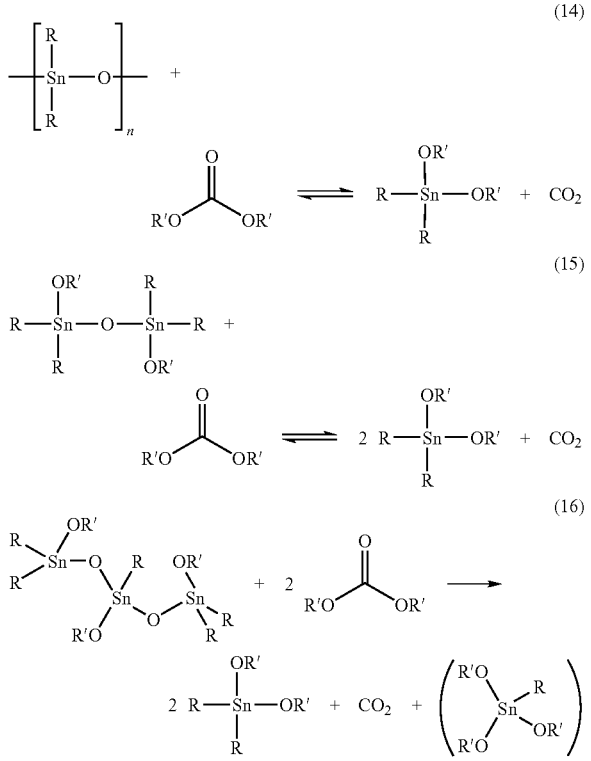

(14)
(15)
(16)

In the case of reacting the alkyltin alkoxide catalyst composition with a mixture of the alcohol and the carbonate, it is thought that all of the above reactions take place concurrently.

It is known that such an alkyltin alkoxide catalyst composition readily reacts with carbon dioxide, forming a complex having a structure in which carbon dioxide is inserted into tin oxygen bonds, and it is thought that the product of the reaction as above contain such an alkyltin alkoxide-carbon dioxide complex. Such complexes are contained in the product originating from the active component, but the carbon dioxide is eliminated during separation by distillation, and hence the product originating from the active component is recovered as the dialkyltin dialkoxide.

As described above, the thermally decomposed matter contains the trialkyltin compound (e.g. a trialkyltin alkoxide) that has a low boiling point and hence can be separated out by distillation. When carrying out reaction as above on the alkyltin alkoxide catalyst composition, the low boiling component trialkyltin alkoxide may thus be removed in advance by distillation, so as to obtain as distillation residue an undistillable alkyltin alkoxide catalyst composition that comprises only the high boiling deactivated component and the active component, before then reacting with the alcohol and/or carbonate.

Next, the reaction conditions will be described. The reactions that take place in step (1) may include equilibrium reactions, and hence the production rate and yield of the product dialkyltin dialkoxide greatly depend on the molar ratio between tin atoms contained in the active component and the alcohol and/or carbonate. Although varying depending on the type of the alcohol and/or carbonate, the ratio of the total number of mols of the alcohol and/or carbonate to the number of mols of tin atoms contained in the active component is generally in a range of from 1 to 1000, preferably 2 to 100. Because the reactions are equilibrium reactions, in the case that excess alcohol is used based on the number of mols of tin atom in the active component contained in the alkyltin alkoxide catalyst composition, reaction can generally be made to proceed more quickly, but if a large excess of the alcohol is used, then much energy is required to evaporate off the alcohol after the reaction, and hence a range as above is preferable. The reaction temperature varies depending on the type of the alcohol and/or carbonate and the reaction pressure, but is generally in a range of from 50 to 200° C. At a high temperature, side reactions are prone to occur, whereas at a low temperature, reaction is very slow; a more preferable temperature range is thus from 60 to 180° C. The reaction pressure also varies depending on the reactant type, and it is possible to carry out the reaction under depressurized or pressurized conditions, although the reaction is preferably carried out in a pressure range of from 20 Pa to 1 MPa. To efficiently remove water and/or carbon dioxide from the reaction system, a more preferable range is from 10 kPa to 0.5 MPa. There are no particular limitations on the reaction time for the reaction carried out in step (1) in the present invention (the residence time in the case of a continuous method), which varies depending on the reaction temperature and pressure, but this reaction time is generally in a range of from 0.001 to 50 hours, preferably from 0.01 to 10 hours, more preferably from 0.1 to 5 hours.

As described above, the reactions that take place in step (1) may include equilibrium reactions, and hence the dialkyltin dialkoxide is obtained by shifting the equilibrium to the product side. That is, the dialkyltin dialkoxide is obtained by removing water and/or carbon dioxide from the reaction liquid. As the dehydration method, a publicly known dehydration method can be used. Examples are distillation, membrane separation, and a method using a dehydrating agent or the like. As distillation, a method such as reduced pressure distillation, pressure distillation, thin film distillation, or azeotropic distillation can be used. As membrane separation, a method such as pervaporation can be used. As a dehydrating agent, a publicly known dehydrating agent such as a molecular sieve can be used. In the case of carrying out reaction using distillation, the reaction is made to proceed while distilling off alcohol containing water and/or carbon dioxide as a low boiling component.

Moreover, an inert gas such a nitrogen or argon may be passed through the reaction liquid so as to promote removal of water and/or carbon dioxide from the reaction liquid. If the inert gas contains water then the alkyltin alkoxide obtained may be hydrolyzed resulting in a decrease in yield, and hence the water content of the inert gas is preferably made to be not more than 0.05 vol %, preferably not more than 0.005 vol %.

There is no need to use a solvent in the reaction, but an inert solvent that undergoes azeotropy with water may be used with an objective of rapidly discharging produced water from the system, or a solvent may be used to improve the fluidity or to facilitate the reaction operation. Examples of such a solvent include chain or cyclic hydrocarbons having from 5 to 16 carbon atoms, and ethers containing a chain or cyclic hydrocarbon having from 4 to 16 carbon atoms. Specific examples include chain or cyclic hydrocarbons having from 6 to 16 carbon atoms selected from pentane (isomers), hexane (isomers), heptane (isomers), octane (isomers), nonane (isomers), decane (isomers), tetradecane (isomers), hexadecane (isomers), cyclohexane, cycloheptane, cyclooctane, benzene, toluene, xylene (isomers), ethylbenzene and so on, and ethers selected from diethyl ether, dipropyl ether (isomers), dibutyl ether (isomers), dihexyl ether (isomers), dioctyl ether (isomers), diphenyl ether and so on.

In the case of using an alcohol having a lower boiling point than water such as methanol or ethanol, if an azeotropic agent that forms an azeotropic composition having a lower boiling point than the alcohol is used, then the dialkyltin dialkoxide can be obtained in the present invention through the method as above, or alternatively production can be similarly be carried out by using a dehydrating agent such as a molecular sieve.

For the above reaction, any reactor may be used, for example although there is no limitation to the following reactors, a batch reactor, a semi-batch reactor, a continuous stirred tank reactor, or a flow reactor, or a combined reactor in which such reactors are connected together. Moreover specifically, the reaction is carried out in a reactor of any type including a stirred tank reactor a multi-stage stirred tank reactor, a packed column, a distillation column, a multi-stage distillation column, a continuous multi-stage distillation column, a reactor having a support therein, or a forced circulation reactor. Publicly known process equipment including instrumentation such as a flow meter and a thermometer, a reboiler, a pump, and a condenser may be attached as required, and heating may be carried out using a publicly known method such as steam or a heater, while cooling may be carried out using a publicly known method such as natural cooling, cooling water or brine.

After the reaction has been carried out, the reaction liquid is subjected to distillation in step (2) so as to distill off and thus recover the dialkyltin dialkoxide from the product originating from the active component. The distillation conditions for the dialkyltin dialkoxide vary according to the type of the alkyl groups and alkoxy groups, but the distillation is generally carried out at a dialkyltin dialkoxide vapor temperature in a range of from 30 to 350° C. The higher the temperature, the more likely thermal decomposition is to occur during the distillation, and hence the distillation is preferably carried out at a temperature in a range of from 30 to 250° C. The pressure varies depending on the type of the dialkyltin dialkoxide, but the distillation is generally carried out under conditions of from normal pressure to a reduced pressure, specifically from 101 kPa to 0.00013 kPa, preferably from 26.6 to 0.0065 kPa. There are no particular limitations on the time for which the distillation is carried out, but this is generally in a range of from 0.001 to 20 hours, preferably from 0.01 to 10 hours, more preferably from 0.1 to 5 hours. For the distillation, a process such as reduced pressure distillation, pressure distillation, or thin film distillation can be used. Furthermore, to improve the efficiency of the distillation, a multi-stage distillation column, a continuous multi-stage distillation column, a packed column or the like may be used. Instrumentation such as a flow meter and a thermometer, valves, piping connecting means, a pump, a heat source and so on may be used attached to the apparatus within a publicly known scope, and moreover heat recovery may be carried out, and the alcohol or the like may be recycled as auxiliary starting material.

According to the above method, the active component can be separated out and recovered as a useful dialkyltin dialkoxide from the undistillable alkyltin alkoxide catalyst composition containing the high boiling deactivated component and the active component.

Examples

Following is a detailed description of the present invention through examples. However, the present invention is not limited to these examples.

Analysis Methods

1) NMR Analysis Method

Apparatus: JNM-A400 FT-NMR system made by JEOL Ltd.

(1) Preparation of $^1$H-NMR/$^{13}$C-NMR/$^{119}$Sn-NMR Analysis Sample 0.3 g of the tin compound was weighed out, and approximately 0.7 g of deuterated chloroform (made by Aldrich, 99.8%) and 0.05 g of tetramethyltin (made by Wako, Wako 1$^{st}$ Grade) as an $^{119}$Sn-NMR internal standard were added, and the solution was mixed to uniformity, thus obtaining an NMR analysis sample.

(2) Quantitative Analysis Method

Quantitative analysis was carried out on the analysis sample solution based on a calibration curve obtained by carrying out analysis on reference samples of various reference substances.

(3) Calculation Method for Alkyltin Alkoxide Yield

The alkyltin alkoxide yield was calculated as mol % produced, this being the number of mols of tin atoms in each alkyltin alkoxide obtained based on the number of mols of tin atoms in the compound represented by chemical formula (1) and/or (5).

2) Analysis Method for Water

Apparatus: CA-05 trace moisture meter made by Mitsubishi Chemical Corporation (1) Quantitative Analysis Method 0.12 ml of the analysis sample was collected using a syringe and the weight was measured, and then the sample was injected as is into the moisture meter and the amount of water was measured. Then, the weight of the syringe was again measured, and hence the amount of the sample injected was calculated, and then the water content in the sample was determined.

3) Gas Chromatography Analysis Method for Carbonate

Apparatus: GC-2010 system made by Shimadzu Corporation, Japan (1) Preparation of Analysis Sample Solution 0.2 g of the reaction solution was weighed out, and approximately 1.5 g of dehydrated acetone was added. Approximately 0.04 g of toluene or diphenyl ether was further added as an internal standard, thus obtaining a gas chromatography analysis sample solution.

(2) Gas Chromatography Analysis Conditions

Column: DB-1 (made by J&W Scientific, USA)
Liquid phase: 100% dimethyl polysiloxane
Length: 30 m
Inside diameter: 0.25 mm
Film thickness: 1 μm
Column temperature: 50° C. (rising by 10° C./min) 300° C.
Injection temperature: 300° C.
Detector temperature: 300° C.
Detection method: FID (3) Quantitative Analysis Method Quantitative analysis was carried out on the analysis sample solution based on a calibration curve obtained by carrying out analysis on reference samples of various reference substances.

Example 1

Step 1: Production of tetraalkyldialkoxydistannoxane 672 g (2.7 mol) of dibutyltin oxide (made by Sankyo Organic Chemicals Co., Ltd., Japan) and 1900 g (21.5 mol) of 3-methyl-1-butanol (made by Kuraray Co., Ltd, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to approximately 145° C., and the flask was immersed in the oil bath and rotation of the evaporator was commenced. With the purge valve of the evaporator left open, rotational agitation and heating were carried out for approximately 40 minutes at normal pressure, whereupon the liquid mixture boiled, and hence distilling off of water-containing 3-methyl-1-butanol began. This state was maintained for 7 hours, and then the purge valve was closed, and the pressure in the system was gradually reduced, and excess 3-methyl-1-butanol was distilled off with the pressure in the system at from 74 to 35 kPa. Once distillate stopped coming off, the flask was lifted out from the oil bath. The reaction liquid was a transparent liquid. After lifting the flask out from the oil bath, the purge valve was gradually opened, so as to return the pressure in the system to normal pressure. 880 g of reaction liquid was obtained in the flask. According to $^{119}$Sn-, $^{1}$H-, and $^{13}$C-NMR analysis results, the product 1,1,3,3-tetrabutyl-1,3-bis(3-methylbutyloxy)-distannoxane was obtained at a yield of 99% based on the dibutyltin oxide. The same procedure was repeated twelve times, thus obtaining a total of 10350 g of 1,1,3,3-tetrabutyl-1,3-bis(3-methylbutyloxy)-distannoxane.

Figure 2:
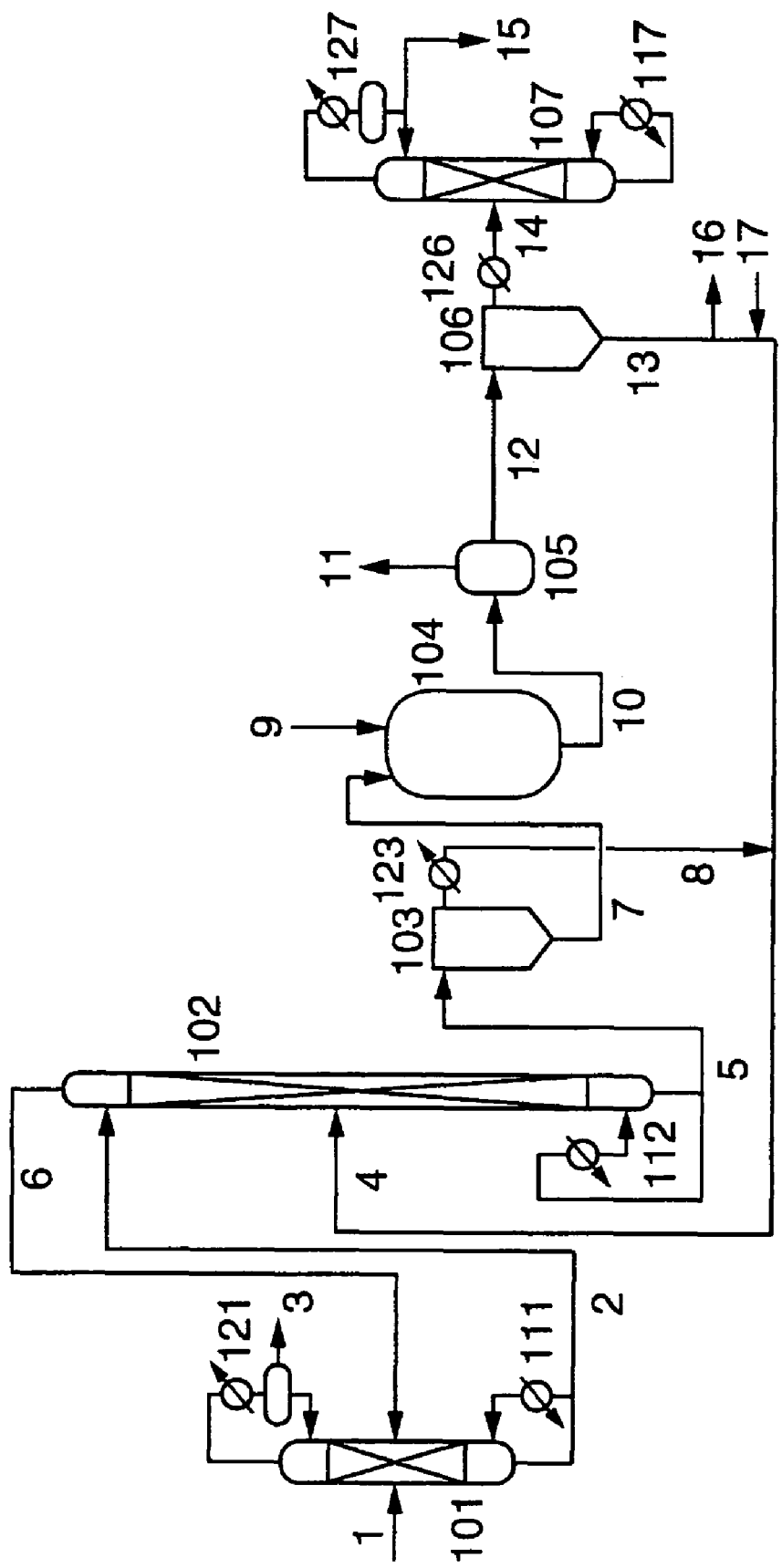
FIG. 2 illustrates a conceptual diagram showing a continuous carbonate production apparatus using an alkyltin alkoxide catalyst composition in the present invention.

Step 2: Production of Carbonate, Obtaining Thermally Decomposed Matter-Containing Alkyltin Alkoxide Catalyst Composition A carbonate was produced using a continuous production apparatus as shown in FIG. 2. The 1,1,3,3-tetrabutyl-1,3-bis(3-methylbutyloxy)-distannoxane produced in step 1 was supplied at 4388 g/Hr from a supply line 4 into a column reactor 102 of inside diameter 151 mm and effective length 5040 mm packed with a Metal Gauze CY packing (made by Sulzer Chemtech Ltd., Switzerland), and 3-methyl-1-butanol (made by Kuraray Co., Ltd, Japan) that had been purified in a distillation column 101 was supplied at 14953 g/Hr from a supply line 2 into the column reactor 102. The liquid temperature in the reactor was adjusted to 160° C. using a heater and a reboiler 112, and the pressure was adjusted to approximately 120 kPa-G using a pressure regulating valve. The residence time in the reactor was approximately 17 minutes. 14953 g/Hr of water-containing 3-methyl-1-butanol was transported from an upper portion of the reactor via a transfer line 6, and 825 g/Hr of 3-methyl-1-butanol (made by Kuraray Co., Ltd, Japan) via a feed line 1, into the distillation column 101 which was packed with a Metal Gauze CY packing (made by Sulzer Chemtech Ltd., Switzerland) and had a reboiler 111 and a condenser 121, whereby purification was carried out by distillation. Distillate containing a high concentration of water from an upper portion of the distillation column 101 was condensed by the condenser 121, and recovered from a recovery line 3. Purified 3-methyl-1-butanol was transported out via the transfer line 2 from a lower portion of the distillation column 101. An alkyltin alkoxide catalyst composition containing dibutyl-bis(3-methylbutyloxy)tin and 1,1,3,3-tetrabutyl-1,3-bis(3-methylbutyloxy)-distannoxane was obtained from a lower portion of the column reactor 102, and was supplied into a thin film evaporator 103 (made by Kobelco Eco-Solutions Co., Ltd., Japan) via a transfer line 5. 3-methyl-1-butanol was evaporated off using the thin film evaporator 103, and returned into the column reactor 102 via a condenser 123, a transfer line 8 and the transfer line 4. The alkyltin alkoxide catalyst composition was transported from a lower portion of the thin film evaporator 103 via a transfer line 7, and was supplied into an autoclave 104, the flow rate of the dibutyl-bis(3-methylbutyloxy)tin and 1,1,3,3-tetrabutyl-1,3-bis(3-methylbutyloxy)-distannoxane active component being adjusted to approximately 5130 g/Hr. Carbon dioxide was supplied at 973 g/Hr into the autoclave via a transfer line 9, the pressure in the autoclave being maintained at 4 MPa-G. The temperature in the autoclave was set to 120° C., the residence time was adjusted to approximately 4 hours, and reaction was carried out between the carbon dioxide and the alkyltin alkoxide catalyst composition, thus obtaining a reaction liquid containing bis(3-methylbutyl)carbonate. The reaction liquid was transferred into a carbon dioxide removal tank 105 via a transfer line 10 and a regulating valve, and residual carbon dioxide was removed, the carbon dioxide being recovered from a transfer line 11. Then, the reaction liquid was transported via a transfer line 12 into a thin film evaporator 106 (made by Kobelco Eco-Solutions Co., Ltd., Japan) set to approximately 142° C. and approximately 0.5 kPa, being supplied in with the 1,1,3,3-tetrabutyl-1,3-bis(3-methylbutyloxy)-distannoxane flow rate adjusted to approximately 4388 g/Hr, and bis(3-methylbutyl)carbonate-containing distillate was obtained, while the evaporation residue was circulated back into the column reactor 102 via a transfer line 13 and the transfer line 4, the 1,1,3,3-tetrabutyl-1,3-bis(3-methylbutyloxy)-distannoxane flow rate being adjusted to approximately 4388 g/Hr. The bis(3-methylbutyl)carbonate-containing distillate was supplied via a condenser 126 and a transfer line 14 at 959 g/Hr into a distillation column 107 which was packed with a Metal Gauze CY packing (made by Sulzer Chemtech Ltd., Switzerland) and had a reboiler 117 and a condenser 127, and distillation purification was carried out, whereby 99 wt % bis(3-methylbutyl)carbonate was obtained from a recovery line 15 at 944 g/Hr. Upon analyzing alkyltin alkoxide catalyst composition from the transfer line 13 by $^{119}$Sn-, $^{1}$H-, and $^{13}$C-NMR, it was found that the alkyltin alkoxide catalyst composition contained 1,1,3,3-tetrabutyl-1,3-bis(3-methylbutyloxy)-distannoxane, but did not contain dibutyl-bis(3-methylbutyloxy)tin. Continuous operation as above was carried out for approximately 240 hours, and then the alkyltin alkoxide catalyst composition was withdrawn from a withdrawal line 16 at 17 g/Hr, while 1,1,3,3-tetrabutyl-1,3-bis(3-methylbutyloxy)-distannoxane produced in step 1 was supplied in from a feed line 17 at 17 g/Hr. Upon withdrawing approximately 120 g of liquid from the withdrawal line 16 and carrying out $^{119}$Sn-NMR analysis, it was found that the liquid contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts were seen in a range of from −240 to −605 ppm for a deactivated component originating from thermal decomposition.

Step 3: Separation and Recovery of Dialkyltin Dialkoxide from Thermally Decomposed Matter-Containing Alkyltin Alkoxide Catalyst Composition 100 g of the thermally decomposed matter-containing alkyltin alkoxide catalyst composition obtained in step 2 and 171 g (0.85 mol) of the bis(3-methylbutyl)carbonate produced in step 2 were mixed together in a 500 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to approximately 150° C., and the flask was immersed in the oil bath and rotation of the evaporator was commenced. With the purge valve of the evaporator left open, rotational agitation was carried out for approximately 3 hours at normal pressure, and then the purge valve was closed, and the pressure in the system was gradually reduced, and residual reactant was distilled off with the pressure in the system at from 20 to 3 kPa. Once distillate stopped coming off, the flask was lifted out from the oil bath. Approximately 117 g of reaction liquid was obtained.

(Separation of Reaction Liquid by Distillation)

Next, using a gas-tight syringe (made by Hamilton), 110 g of the reaction liquid was put into a 200 ml three-neck flask equipped with a three-way stopcock, a reflux condenser-equipped fractionating column in which a 45 cm-long distillation column packed with Heli-Pak No. 3 and a distillate receiver were connected together, and a thermometer, while passing in 0.3 L/min of nitrogen gas via the three-way stopcock. The flask was immersed in an oil bath heated to approximately 185° C. After carrying out stirring and heating for approximately 20 minutes, the temperature of the reaction liquid had reached approximately 177° C. The pressure in the apparatus was then gradually reduced, and distillation was carried out at approximately 0.06 kPa. Distillate 1 was recovered at approximately 0.5 mL/min. After the distillate 1 stopped coming off, the pressure in the apparatus was further gradually reduced to approximately 0.01 kPa and the distillation was continued, whereby distillate 2 was recovered at approximately 0.5 mL/min. The distillate stopped coming off after approximately 2 hours, and then the reduced pressure in the apparatus was released, and the heating was stopped, thus stopping the distillation. The amounts of the distillate 1 and distillate 2 obtained and the residual matter in the flask were respectively 33, 56, and 20 g. NMR analysis was carried out on each of the distillate 1, the distillate 2, and the residual matter in the flask. Distillate 1 was found to contain 88 wt % of tributyl-(3-methylbutyloxy)-tin and 12 wt % of bis(3-methylbutyl)carbonate, distillate 2 was found to contain 98% of dibutyl-bis(3-methylbutyloxy)-tin, and the residual matter in the flask was found to contain approximately 1 wt % of 1,1,3,3-tetrabutyl-1,3-bis(3-methylbutyloxy)-distannoxane with a plurality of NMR shifts originating from the high boiling deactivated component also being seen in a range of from −240 to −605 ppm.

Example 2

Production of Carbonate, Obtaining Thermally Decomposed Matter-Containing Alkyltin Alkoxide Catalyst Composition A thermally decomposed matter-containing alkyltin alkoxide catalyst composition was obtained through the same process as in steps 1 and 2 of Example 1. The $^{119}$Sn-NMR analysis results were that the thermally decomposed matter-containing alkyltin alkoxide catalyst composition contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts originating from a high boiling deactivated component were seen in a range of from −240 to −605 ppm.

(Separation and Recovery of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 180° C. and a pressure of approximately 0.06 kPa. This low boiling component contained 98 wt % of tributyl(3-methylbutyloxy)tin. Approximately 386 g of a high boiling component was obtained, and upon carrying out $^{119}$Sn-NMR analysis thereon, this was found to contain 1,1,3,3-tetrabutyl-1,3-bis(3-methylbutyloxy)distannoxane, with a plurality of NMR shifts originating from the deactivated component also being seen in a range of from −240 to −605 ppm. The high boiling component was mixed with 855 g (4.23 mol) of the bis(3-methylbutyl)carbonate produced in step 2 of Example 1, and reaction was carried out for 4 hours at 140° C. Then, the reaction liquid was supplied at 300 g/Hr into a molecular distillation apparatus, and residual carbonate was separated off at a temperature of approximately 140° C. and a pressure of approximately 0.5 kPa, and approximately 462 g of a high boiling component was recovered. Next, using a gas-tight syringe (made by Hamilton), 400 g of the high boiling component was put into a 500 mL three-neck flask equipped with a three-way stopcock, a condenser, a distillate receiver and a thermometer, while passing in 0.3 L/min of nitrogen gas via the three-way stopcock. The flask was immersed in an oil bath heated to approximately 175° C. The pressure in the apparatus was gradually reduced, and distillation was carried out at approximately 0.01 kPa. 376 g of a low boiling component was obtained, this containing 98 wt % of dibutyl-bis(3-methylbutyloxy)tin according to the results of $^{119}$Sn-NMR analysis. The residual matter in the flask contained approximately 1 wt % of 1,1,3,3-tetrabutyl-1,3-bis(3-methylbutyloxy)-distannoxane with a plurality of NMR shifts originating from the high boiling deactivated component also being seen in a range of from −240 to −605 ppm.

Example 3

Production of Carbonate, Obtaining Thermally Decomposed Matter-Containing Alkyltin Alkoxide Catalyst Composition A thermally decomposed matter-containing alkyltin alkoxide catalyst composition was obtained through the same process as in steps 1 and 2 of Example 1. The $^{119}$Sn-NMR analysis results were that the thermally decomposed matter-containing alkyltin alkoxide catalyst composition contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts originating from a high boiling deactivated component were seen in a range of from −240 to −605 ppm.

(Separation and Recovery of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 180° C. and a pressure of approximately 0.06 kPa. This low boiling component contained 99 wt % of tributyl(3-methylbutyloxy)tin. Approximately 386 g of a high boiling component was obtained, and upon carrying out $^{119}$Sn-NMR analysis thereon, this was found to contain 1,1,3,3-tetrabutyl-1,3-bis(3-methylbutyloxy)distannoxane, with a plurality of NMR shifts originating from the high boiling deactivated component also being seen in a range of from −240 to −605 ppm. The high boiling component was mixed with 855 g (4.23 mol) of the bis(3-methylbutyl)carbonate produced in step 2 of Example 1 in a flask under a nitrogen atmosphere, and reaction was carried out for 4 hours at 140° C. and normal pressure. Then, the reaction liquid was supplied at 300 g/Hr into a molecular distillation apparatus, and residual carbonate was separated off at a temperature of approximately 140° C. and a pressure of approximately 0.5 kPa, a high boiling component being recovered. The high boiling component was supplied at 300 g/Hr into a molecular distillation apparatus, and separation by distillation was carried out at a temperature of approximately 190° C. and a pressure of approximately 0.01 kPa, whereupon 374 g of a low boiling component was obtained. The low boiling component contained 98 wt % of dibutyl-bis(3-methylbutyloxy)tin. On the other hand, for the high boiling component, a plurality of NMR shifts originating from the high boiling deactivated component were seen in a range of from −240 to −605 ppm.

Example 4

Production of Carbonate, Obtaining Thermally Decomposed Matter-Containing Alkyltin Alkoxide Catalyst Composition A thermally decomposed matter-containing alkyltin alkoxide catalyst composition was obtained through the same process as in steps 1 and 2 of Example 1. The $^{119}$Sn-NMR analysis results were that the thermally decomposed matter-containing alkyltin alkoxide catalyst composition contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts originating from a high boiling deactivated component were seen in a range of from −240 to −605 ppm.

(Separation and Recovery of Dialkyltin Dialkoxide from Thermally Decomposed Matter-Containing Alkyltin Alkoxide Catalyst Composition)

Using a gas-tight syringe (made by Hamilton), 500 g of the above thermally decomposed matter-containing alkyltin alkoxide catalyst composition was put into a 500 mL three-neck flask equipped with a three-way stopcock, a condenser, a distillate receiver and a thermometer, while passing in 0.3 L/min of nitrogen gas via the three-way stopcock. The flask was immersed in an oil bath heated to approximately 185° C. The pressure in the apparatus was then gradually reduced, and distillation was carried out at approximately 0.06 kPa. 116 g of a low boiling component was obtained, this containing 99 wt % of tributyl-(3-methylbutyloxy)tin according to the results of $^{119}$Sn-NMR analysis. The amount of residual matter in the flask was 385 g, this containing approximately 77 wt % of 1,1,3,3-tetrabutyl-1,3-bis(3-methylbutyloxy)-distannoxane and further exhibiting a plurality of NMR shifts originating from the high boiling deactivated component in a range of from −240 to −605 ppm according to the results of $^{119}$Sn-NMR analysis. The residual matter in the flask was mixed with 855 g (4.23 mol) of the bis(3-methylbutyl)carbonate produced in step 2 of Example 1, and reaction was carried out for 4 hours at 140° C. Then, the reaction liquid was supplied at 300 g/Hr into a molecular distillation apparatus, and residual carbonate was separated off at a temperature of approximately 140° C. and a pressure of approximately 0.4 kPa, a high boiling component being recovered. The high boiling component was supplied at 300 g/Hr into a molecular distillation apparatus, and separation by distillation was carried out at a temperature of approximately 190° C. and a pressure of approximately 0.01 kPa, whereupon 374 g of a low boiling component was obtained. The low boiling component contained 98 wt % of dibutyl-bis(3-methylbutyloxy)

tin. On the other hand, for the high boiling component, a plurality of NMR shifts originating from the high boiling deactivated component were seen in a range of from −240 to −605 ppm.

Example 5

Step 1: Production of tetraalkyldialkoxydistannoxane 672 g (2.7 mol) of dibutyltin oxide (made by Sankyo Organic Chemicals Co., Ltd., Japan) and 1700 g (16.7 mol) of 2-ethyl-1-butanol (made by Chisso Corporation, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to approximately 157° C., and the flask was immersed in the oil bath and rotation of the evaporator was commenced. With the purge valve of the evaporator left open, rotational agitation and heating were carried out for approximately 40 minutes at normal pressure, and then the purge valve was closed, and the pressure in the system was gradually reduced, and then with the pressure in the system at from 80 to 65 kPa, reaction was continued for approximately 5 hours while distilling off water-containing 2-ethyl-1-butanol. Then, the pressure in the system was further reduced and the distillation was continued, and then once distillate stopped coming off, the flask was lifted out from the oil bath. The reaction liquid was a transparent liquid. After lifting the flask out from the oil bath, the purge valve was gradually opened, so as to return the pressure in the system to normal pressure. 928 g of reaction liquid was obtained in the flask. According to $^{119}$Sn-, $^{1}$H-, and $^{13}$C-NMR analysis results, the product 1,1,3,3-tetrabutyl-1,3-bis(2-ethylbutyloxy)-distannoxane was obtained at a yield of 99% based on the dibutyltin oxide. The same procedure was repeated twelve times, thus obtaining a total of 11200 g of 1,1,3,3-tetrabutyl-1,3-bis(2-ethylbutyloxy)-distannoxane.

Step 2: Production of Carbonate, Obtaining Thermally Decomposed Matter-Containing Alkyltin Alkoxide Catalyst Composition A carbonate was produced using a continuous production apparatus as shown in FIG. 2. The 1,1,3,3-tetrabutyl-1,3-bis(2-ethylbutyloxy)-distannoxane produced in step 1 was supplied at 4566 g/Hr from a supply line 4 into a column reactor 102 of inside diameter 151 mm and effective length 5040 mm packed with a Metal Gauze CY packing (made by Sulzer Chemtech Ltd., Switzerland), and 2-ethyl-1-butanol (made by Chisso Corporation, Japan) that had been purified in the distillation column 101 was supplied at 12260 g/Hr from a supply line 2 into the column reactor 102. The liquid temperature in the reactor was adjusted to 160° C. using a heater and a reboiler 112, and the pressure was adjusted to approximately 32 kPa-G using a pressure regulating valve. The residence time in the reactor was approximately 17 minutes. 12260 g/Hr of water-containing 2-ethyl-1-butanol was transported from an upper portion of the reactor via a transfer line 6, and 958 g/Hr of 2-ethyl-1-butanol (made by Chisso Corporation, Japan) was transported via a feed line 1, into the distillation column 101 which was packed with a Metal Gauze CY packing (made by Sulzer Chemtech Ltd., Switzerland) and had a reboiler 111 and a condenser 121, whereby purification was carried out by distillation. Distillate containing a high concentration of water from an upper portion of the distillation column 101 was condensed by the condenser 121, and recovered from a recovery line 3. Purified 2-ethyl-1-butanol was transported out via the transfer line 2 from a lower portion of the distillation column 101. An alkyltin alkoxide catalyst composition containing dibutyl-bis(2-ethylbutyloxy)tin and 1,1,3,3-tetrabutyl-1,3-bis(2-ethylbutyloxy)-distannoxane was obtained from a lower portion of the column reactor 102, and was supplied into a thin film evaporator 103 (made by Kobelco Eco-Solutions Co., Ltd., Japan) via a transfer line 5. 2-ethyl-1-butanol was evaporated off using the thin film evaporator 103, and returned into the column reactor 102 via a condenser 123, a transfer line 8 and the transfer line 4. The alkyltin alkoxide catalyst composition was transported from a lower portion of the thin film evaporator 103 via a transfer line 7, and was supplied into an autoclave 104, the flow rate of the dibutyl-bis(2-ethylbutyloxy)tin and 1,1,3,3-tetrabutyl-1,3-bis(2-ethylbutyloxy)-distannoxane active component being adjusted to approximately 5442 g/Hr. Carbon dioxide was supplied at 973 g/Hr into the autoclave via a transfer line 9, the pressure in the autoclave being maintained at 4 MPa-G. The temperature in the autoclave was set to 120° C., the residence time was adjusted to approximately 4 hours, and reaction was carried out between the carbon dioxide and the alkyltin alkoxide catalyst composition, thus obtaining a reaction liquid containing bis(2-ethylbutyl)carbonate. The reaction liquid was transferred into a carbon dioxide removal tank 105 via a transfer line 10 and a regulating valve, and residual carbon dioxide was removed, the carbon dioxide being recovered from a transfer line 11. Then, the reaction liquid was transported via a transfer line 12 into a thin film evaporator 106 (made by Kobelco Eco-Solutions Co., Ltd., Japan) set to 140° C. and approximately 1.3 kPa, being supplied in with the 1,1,3,3-tetrabutyl-1,3-bis(2-ethylbutyloxy)-distannoxane flow rate adjusted to approximately 4566 g/Hr, and bis(2-ethylbutyl)carbonate-containing distillate was obtained, while the evaporation residue was circulated back into the column reactor 102 via a transfer line 13 and the transfer line 4, the 1,1,3,3-tetrabutyl-1,3-bis(2-ethylbutyloxy)-distannoxane flow rate being adjusted to approximately 4566 g/Hr. The bis(2-ethylbutyl)carbonate-containing distillate was supplied via a condenser 126 and a transfer line 14 at 1090 g/Hr into a distillation column 107 which was packed with a Metal Gauze CY packing (made by Sulzer Chemtech Ltd., Switzerland) and had a reboiler 117 and a condenser 127, and distillation purification was carried out, whereby 99 wt % bis(2-ethylbutyl)carbonate was obtained from a recovery line 15 at 1075 g/Hr. Upon analyzing alkyltin alkoxide catalyst composition from the transfer line 13 by $^{119}$Sn-, $^{1}$H-, and $^{13}$C-NMR, it was found that the alkyltin alkoxide catalyst composition contained 1,1,3,3-tetrabutyl-1,3-bis(2-ethylbutyloxy)-distannoxane, but did not contain dibutyl-bis(2-ethylbutyloxy)tin. Continuous operation as above was carried out for approximately 160 hours, and then the alkyltin alkoxide catalyst composition was withdrawn from a withdrawal line 16 at 23 g/Hr, while 1,1,3,3-tetrabutyl-1,3-bis(2-ethylbutyloxy)-distannoxane produced in step 1 was supplied in from a feed line 17 at 23 g/Hr. Upon withdrawing approximately 120 g of liquid from the withdrawal line 16 and carrying out $^{119}$Sn-NMR analysis, it was found that the liquid contained approximately 60 wt % of 1,1,3,3-tetrabutyl-1,3-bis(2-ethylbutyloxy)-distannoxane, and in addition to this there was tributyl(2-ethylbutyloxy)tin and a plurality of NMR shifts originating from a high boiling deactivated component were seen in a range of from −240 to −605 ppm.

Step 3: Separation and Recovery of Dialkyltin Dialkoxide from Thermally Decomposed Matter-Containing Alkyltin Alkoxide Catalyst Composition 100 g of the thermally decomposed matter-containing alkyltin alkoxide catalyst composition obtained in step 2 and 202 g (0.88 mol) of the bis(2-ethylbutyl)carbonate produced in step 2 were mixed together, in a 500 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to 150° C., and the flask was immersed in the oil bath and rotation of the evaporator was commenced. With the purge valve of the evaporator left open, rotational agitation was carried out for approximately 3 hours at normal pressure, and then the purge valve was closed, and the pressure in the system was gradually reduced, and residual reactant was distilled off with the pressure in the system at from 20 to 0.3 kPa. Once distillate stopped coming off, the flask was lifted out from the oil bath. Approximately 119 g of reaction liquid was obtained.

(Separation of Reaction Liquid by Distillation)

Next, using a gas-tight syringe (made by Hamilton), 115 g of the reaction liquid was put into a 200 ml three-neck flask equipped with a three-way stopcock, a reflux condenser-equipped fractionating column in which a 45 cm-long distillation column packed with Heli-Pak No. 3 and a distillate receiver were connected together, and a thermometer, while passing in 0.3 L/min of nitrogen gas via the three-way stopcock. The flask was immersed in an oil bath heated to approximately 195° C. Stirring and heating were carried out for approximately 20 minutes, and then the pressure in the apparatus was gradually reduced, and distillation was carried out at approximately 0.06 kPa. Distillate 1 was recovered at approximately 0.5 mL/min. After the distillate 1 stopped coming off, the pressure in the apparatus was further gradually reduced to approximately 0.01 kPa and the distillation was continued, whereby distillate 2 was recovered at approximately 0.5 mL/min. The distillate stopped coming off after approximately 2 hours, and then the reduced pressure in the apparatus was released, and the heating was stopped, thus stopping the distillation. The amounts of the distillate 1 and distillate 2 obtained and the residual matter in the flask were respectively 35, 56, and 21 g. NMR analysis was carried out on each of the distillate 1, the distillate 2, and the residual matter in the flask. Distillate 1 was found to contain 87 wt % of tributyl-(2-ethylbutyloxy)-tin and 13 wt % of bis(2-ethylbutyl)carbonate, distillate 2 was found to contain 97% of dibutyl-bis(2-ethylbutyloxy)-tin, and the residual matter in the flask was found to contain approximately 1 wt % of 1,1,3,3-tetrabutyl-1,3-bis(2-ethylbutyloxy)-distannoxane with a plurality of NMR shifts originating from the high boiling deactivated component also being seen in a range of from −240 to −605 ppm.

Example 6

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 5. The $^{119}$Sn-NMR analysis results were that the thermally decomposed matter-containing alkyltin alkoxide catalyst composition contained approximately 60 wt % of 1,1,3,3-tetrabutyl-1,3-bis(2-ethylbutyloxy)-distannoxane, and in addition to this there was tributyl(2-ethylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

100 g of the above thermally decomposed matter-containing alkyltin alkoxide catalyst composition and 1795 g (17.6 mol) of 2-ethyl-1-butanol (made by Chisso Corporation, Japan) were mixed together in a 3000 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to 160° C., and the flask was immersed in the oil bath and rotation of the evaporator was commenced. With the purge valve of the evaporator left open, rotational agitation was carried out for approximately 3 hours at normal pressure, and then the purge valve was closed, and the pressure in the system was gradually reduced, and residual reactant was distilled off with the pressure in the system at from 20 to 0.3 kPa. Once distillate stopped coming off, the flask was lifted out from the oil bath. Approximately 118 g of reaction liquid was obtained.

(Separating Out of Dialkyltin Dialkoxide by Distillation)

Next, using a gas-tight syringe (made by Hamilton), 113 g of the reaction liquid was put into a 200 ml three-neck flask equipped with a three-way stopcock, a reflux condenser-equipped fractionating column in which a 45 cm-long distillation column packed with Heli-Pak No. 3 and a distillate receiver were connected together, and a thermometer, while passing in 0.3 L/min of nitrogen gas via the three-way stopcock. The flask was immersed in an oil bath heated to approximately 195° C. Stirring and heating were carried out for approximately 20 minutes, and then the pressure in the apparatus was gradually reduced, and distillation was carried out at approximately 0.06 kPa. Distillate 1 was recovered at approximately 0.5 mL/min. After the distillate 1 stopped coming off, the pressure in the apparatus was further gradually reduced to approximately 0.01 kPa and the distillation was continued, whereby distillate 2 was recovered at approximately 0.5 mL/min. The distillate stopped coming off after approximately 2 hours, and then the reduced pressure in the apparatus was released, and the heating was stopped, thus stopping the distillation. The amounts of the distillate 1 and distillate 2 obtained and the residual matter in the flask were respectively 34, 55, and 21 g. NMR analysis was carried out on each of distillate 1, the distillate 2, and the residual matter in the flask. Distillate 1 was found to contain 96 wt % of tributyl-(2-ethylbutyloxy)-tin and 4 wt % of 2-ethyl-1-butanol, distillate 2 was found to contain 97% of dibutyl-bis(2-ethylbutyloxy)-tin, and the residual matter in the flask was found to contain approximately 4 wt % of 1,1,3,3-tetrabutyl-1,3-bis(2-ethylbutyloxy)-distannoxane with a plurality of NMR shifts originating from the high boiling deactivated component also being seen in a range of from −240 to −605 ppm.

Example 7

Step 1: Production of tetraalkyldialkoxydistannoxane 692 g (2.78 mol) of dibutyltin oxide (made by Sankyo Organic Chemicals Co., Ltd., Japan) and 2000 g (27 mol) of 1-butanol (made by Wako, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 126° C., and the flask was immersed in the oil bath and rotation of the evaporator was commenced. With the purge valve of the evaporator left open, rotational agitation and heating were carried out for approximately 30 minutes at normal pressure, whereupon the liquid mixture boiled, and hence distilling off of a low boiling component began. This state was maintained for 8 hours, and then the purge valve was closed, and the pressure in the system was gradually reduced, and residual low boiling component was distilled off with the pressure in the system at from 76 to 54 kPa. Once low boiling component stopped coming off, the flask was lifted out from the oil bath. The reaction liquid was a transparent liquid. After lifting the flask out from the oil bath, the purge valve was gradually opened, so as to return the pressure in the system to normal pressure. 952 g of reaction liquid was obtained in the flask. According to $^{119}$Sn-, $^{1}$H-, and $^{13}$C-NMR analysis results, the product 1,1,3,3-tetrabutyl-1,3-di(butyloxy)-distannoxane was obtained at a yield of 99% based on the dibutyltin oxide. The same procedure was repeated twelve times, thus obtaining a total of 11500 g of 1,1,3,3-tetrabutyl-1,3-di(butyloxy)-distannoxane.

Step 2: Production of Carbonate, Obtaining Thermally Decomposed Matter-Containing Alkyltin Alkoxide Catalyst Composition A carbonate was produced using a continuous production apparatus as shown in FIG. 2. The 1,1,3,3-tetrabutyl-1,3-di(butyloxy)-distannoxane produced in step 1 was supplied at 4201 g/Hr from a supply line 4 into a column reactor 102 of inside diameter 151 mm and effective length 5040 mm packed with a Mellapak 750Y packing (made by Sulzer Chemtech Ltd., Switzerland), and 1-butanol (made by Wako, Japan) that had been purified in a distillation column 101 was supplied at 24717 g/Hr from a supply line 2 into the column reactor 102. The liquid temperature in the reactor was adjusted to 160° C. using a heater and a reboiler 112, and the pressure was adjusted to approximately 250 kPa-G using a pressure regulating valve. The residence time in the reactor was approximately 10 minutes. 24715 g/Hr of water-containing 1-butanol was transported from an upper portion of the reactor via a transfer line 6, and 824 g/Hr of 1-butanol (made by Wako, Japan) via a supply line 1, into the distillation column 101 which was packed with a Metal Gauze CY packing (made by Sulzer Chemtech Ltd., Switzerland) and had a reboiler 111 and a condenser 121, whereby purification was carried out by distillation. Distillate containing a high concentration of water from an upper portion of the distillation column 101 was condensed by the condenser 121, and recovered from a recovery line 3. Purified 1-butanol was transported out via the transfer line 2 from a lower portion of the distillation column 101. An alkyltin alkoxide catalyst composition containing dibutyltin dibutoxide and 1,1,3,3-tetrabutyl-1,3-di(butyloxy)-distannoxane was obtained from a lower portion of the column reactor 102, and was supplied into a thin film evaporator 103 (made by Kobelco Eco-Solutions Co., Ltd., Japan) via a transfer line 5. 1-Butanol was evaporated off using the thin film evaporator 103, and returned into the column reactor 102 via a condenser 123, a transfer line 8 and the transfer line 4. The alkyltin alkoxide catalyst composition was transported from a lower portion of the thin film evaporator 103 via a transfer line 7, and was supplied into an autoclave 104, the flow rate of the dibutyltin dibutoxide and 1,1,3,3-tetrabutyl-1,3-di(butyloxy)-distannoxane active component being adjusted to approximately 4812 g/Hr. Carbon dioxide was supplied at 973 g/Hr into the autoclave via a supply line 9, the pressure in the autoclave being maintained at 4 MPa-G. The temperature in the autoclave was set to 120° C., the residence time was adjusted to approximately 4 hours, and reaction was carried out between the carbon dioxide and the alkyltin alkoxide catalyst composition, thus obtaining a reaction liquid containing dibutyl carbonate. The reaction liquid was transferred into a carbon dioxide removal tank 105 via a transfer line 10 and a regulating valve, and residual carbon dioxide was removed, the carbon dioxide being recovered from, a transfer line 11. Then, the reaction liquid was transported via a transfer line 12 into a thin film evaporator 106 (made by Kobelco Eco-Solutions Co., Ltd., Japan) set to 140° C. and approximately 1.4 kPa, being supplied in with the 1,1,3,3-tetrabutyl-1,3-di(butyloxy)-distannoxane flow rate adjusted to approximately 4201 g/Hr, and dibutyl carbonate-containing distillate was obtained, while the evaporation residue was circulated back into the column reactor 102 via a transfer line 13 and the transfer line 4, the 1,1,3,3-tetrabutyl-1,3-di(butyloxy)-distannoxane flow rate being adjusted to approximately 4201 g/Hr. The dibutyl carbonate-containing distillate was supplied via a condenser 126 and a transfer line 14 at 830 g/Hr into a distillation column 107 which was packed with a Metal Gauze CY packing (made by Sulzer Chemtech Ltd., Switzerland) and had a reboiler 117 and a condenser 127, and distillation purification was carried out, whereby 99 wt % dibutyl carbonate was obtained from a recovery line 15 at 814 g/Hr. Upon analyzing alkyltin alkoxide catalyst composition from the transfer line 13 by $^{119}$Sn-, $^{1}$H-, and $^{13}$C-NMR, it was found that the alkyltin alkoxide catalyst composition contained 1,1,3,3-tetrabutyl-1,3-di(butyloxy)-distannoxane, but did not contain dibutyltin dibutoxide. Continuous operation as above was carried out for approximately 600 hours, and then the alkyltin alkoxide catalyst composition was withdrawn from a withdrawal line 16 at 16 g/Hr, while 1,1,3,3-tetrabutyl-1,3-di(butyloxy)-distannoxane produced in step 1 was supplied in from a feed line 17 at 16 g/Hr. Upon withdrawing approximately 120 g of liquid from the withdrawal line 16 and carrying out $^{119}$Sn-NMR analysis, it was found that the liquid contained approximately 60 wt % of 1,1,3,3-tetrabutyl-1,3-di(butyloxy)-distannoxane, and in addition to this there was tributyltin butoxide and a plurality of NMR shifts originating from a high boiling deactivated component were seen in a range of from −240 to −605 ppm.

Step 3: Obtaining of Dialkyltin Dialkoxide from Thermally Decomposed Matter-Containing Alkyltin Alkoxide Catalyst Composition 100 g of the thermally decomposed matter-containing alkyltin alkoxide catalyst composition obtained in step 2 and 233 g (1.34 mol) of the dibutyl carbonate produced in step 2 were mixed together in a 500 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to approximately 150° C., and the flask was immersed in the oil bath and rotation of the evaporator was commenced. With the purge valve of the evaporator left open, rotational agitation was carried out for approximately 3 hours at normal pressure, and then the purge valve was closed, and the pressure in the system was gradually reduced, and residual reactant was distilled off with the pressure in the system at from 20 to 3 kPa. Once distillate stopped coming off, the flask was lifted out from the oil bath. Approximately 117 g of reaction liquid was obtained.

(Separation of Reaction Liquid by Distillation)

Next, using a gas-tight syringe (made by Hamilton), 110 g of the reaction liquid was put into a 200 ml three-neck flask equipped with a three-way stopcock, a reflux condenser-equipped fractionating column in which a 45 cm-long distillation column packed with Heli-Pak No. 3 and a distillate receiver were connected together, and a thermometer, while passing in 0.3 L/min of nitrogen gas via the three-way stopcock. The flask was immersed in an oil bath heated to approximately 175° C. After carrying out stirring and heating for approximately 20 minutes, the temperature of the reaction liquid had reached approximately 167° C. The pressure in the apparatus was then gradually reduced, and distillation was carried out at approximately 0.2 kPa. Distillate 1 was recovered at approximately 0.5 mL/min. After the distillate 1 stopped coming off, the pressure in the apparatus was further gradually reduced to approximately 0.03 kPa and the distillation was continued, whereby distillate 2 was recovered at approximately 0.5 mL/min. The distillate stopped coming off after approximately 2 hours, and then the reduced pressure in the apparatus was released, and the heating was stopped, thus stopping the distillation. The amounts of the distillate 1 and distillate 2 obtained and the residual matter in the flask were respectively 33, 56, and 20 g. NMR analysis was carried out on each of the distillate 1, the distillate 2, and the residual matter in the flask. Distillate 1 was found to contain 90 wt % of tributyltin butoxide and 10 wt % of dibutyl carbonate, and as distillate 2 98% of dibutyltin dibutoxide was obtained. The residual matter in the flask was found to contain approximately 1 wt % of 1,1,3,3-tetrabutyl-1,3-di(butyloxy)-distannoxane with a plurality of NMR shifts originating from the high boiling deactivated component also being seen in a range of from −240 to −605 ppm.

Example 8

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 1. The $^{119}$Sn-NMR analysis results were that the thermally decomposed matter-containing alkyltin alkoxide catalyst composition contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

Figure 3:
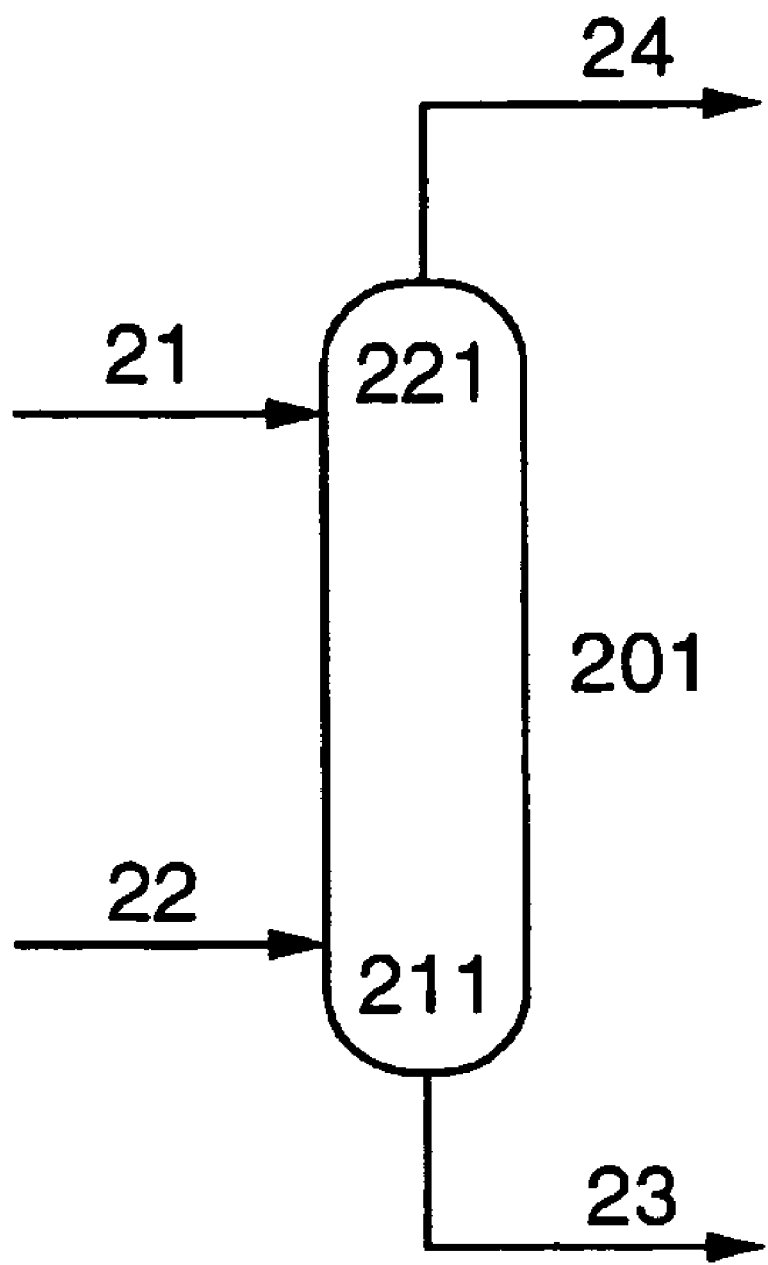
FIG. 3 illustrates a conceptual diagram of an example of a column reactor used in the present invention.

500 g of the above thermally decomposed matter-containing alkyltin alkoxide catalyst composition was supplied at approximately 300 g/Hr into a molecular distillation apparatus (MS-300, made by Sibata Scientific Technology Ltd., Japan), and a volatile component was removed at a temperature of approximately 190° C. and a pressure of approximately 0.06 kPa. This low boiling component contained 98 wt % of tributyl(3-methylbutyloxy)tin. Approximately 385 g of a high boiling component was obtained, and upon carrying out $^{119}$Sn-NMR analysis thereon, this was found to contain 1,1,3,3-tetrabutyl-1,3-bis(3-methylbutyloxy)distannoxane, with a plurality of NMR shifts originating from the high boiling deactivated component also being seen in a range of from −240 to −605 ppm. 64 g of the high boiling component was mixed with 1342 g of 3-methyl-1-butanol (made by Kuraray Co., Ltd, Japan), and the liquid mixture was subjected to reaction at 140° C. in a column reactor 201 as shown in FIG. 3. Heli-pak No. 3 (made by Tokyo Tokushu Kanaami, Japan) was packed into a SUS316 tube reactor of inside diameter 15 mm and total length 1635 mm (effective length 1450 mm) having a supply line 21 and a low boiling component recovery line 24 attached to an upper portion 221 of the reactor, and a supply line 22 and a recovery line 23 attached to a lower portion 211 of the reactor, and the tube reactor was heated using a heater set to 150° C. The liquid mixture was supplied in at 30 g/Hr via the supply line 21 using a liquid feeding pump, and carbon dioxide gas was supplied in at 80 ml/min from the supply line 22. The residence time in the reactor was approximately 25 minutes. A low boiling component containing water and 3-methyl-1-butanol was withdrawn from the low boiling component recovery line 24 in a gaseous form, and a high boiling component began to flow out from the recovery line 23. Operation was continued in this state with continuous liquid feeding and continuous withdrawal, whereby approximately 870 g of the high boiling component was recovered. Then, the high boiling component was supplied at 300 g/Hr into a molecular distillation apparatus, and residual 3-methyl-1-butanol was separated off at a temperature of approximately 130° C. and a pressure of approximately 2 kPa, and approximately 78 g of liquid was recovered as a high boiling component. The liquid was supplied at 100 g/Hr into a molecular distillation apparatus, and separation by distillation was carried out at a temperature of approximately 200° C. and a pressure of approximately 0.01 kPa, whereby 63 g of a low boiling component was obtained. The low boiling component contained 98 wt % of dibutyl-bis (3-methylbutyloxy)tin. On the other hand, for the high boiling component, a plurality of NMR shifts originating from the high boiling deactivated component were seen in a range of from −240 to −605 ppm.

Example 9

Step 1: Production of tetraalkyldialkoxydistannoxane 700 g (1.94 mol) of dioctyltin oxide (made by Sankyo Organic Chemicals Co., Ltd., Japan) and 1700 g (19.3 mol) of 3-methyl-1-butanol (made by Kuraray Co., Ltd, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 143° C., and the flask was immersed in the oil bath and rotation of the evaporator was commenced. With the purge valve of the evaporator left open, rotational agitation and heating were carried out for approximately 40 minutes at normal pressure, whereupon the liquid mixture boiled, and hence distilling off of a low boiling component began. This state was maintained for 7 hours, and then the purge valve was closed, and the pressure in the system was gradually reduced, and residual low boiling component was distilled off with the pressure in the system at from 76 to 32 kPa. Once low boiling component stopped coming off, the flask was lifted out from the oil bath. The reaction liquid was a transparent liquid. After lifting the flask out from the oil bath, the purge valve was gradually opened, so as to return the pressure in the system to normal pressure. 864 g of reaction liquid was obtained in the flask; According to $^{119}$Sn-, $^{1}$H-, and $^{13}$C-NMR analysis results, the product 1,1,3,3-tetraoctyl-1, 3-bis(3-methylbutyloxy)-distannoxane was obtained at a yield of 99% based on the dioctyltin oxide. The same procedure was repeated twelve times, thus obtaining a total of 10350 g of 1,1,3,3-tetraoctyl-1,3-bis(3-methylbutyloxy)-distannoxane.

Step 2: Production of Carbonate, Obtaining Thermally Decomposed Matter-Containing Alkyltin Alkoxide Catalyst Composition A carbonate was produced using a continuous production apparatus as shown in FIG. 2. The 1,1,3,3-tetraoctyl-1,3-bis (3-methylbutyloxy)-distannoxane produced in step 1 was supplied, at 5887 g/Hr from a supply line 4 into a column reactor 102 of inside diameter 151 mm and effective length 5040 mm packed with a Metal Gauze CY packing (made by Sulzer Chemtech Ltd., Switzerland), and 3-methyl-1-butanol (made by Kuraray Co., Ltd, Japan) that had been purified in a distillation column 101 was supplied at 14953 g/Hr from a supply line 2 into the column reactor 102. The liquid temperature in the reactor was adjusted to 160° C. using a heater and a reboiler 112, and the pressure was adjusted to approximately 120 kPa-G using a pressure regulating valve. The residence time in the reactor was approximately 17 minutes. 14950 g/Hr of water-containing 3-methyl-1-butanol was transported from an upper portion of the reactor via a transfer line 6, and 824 g/Hr of 3-methyl-1-butanol (made by Kuraray Co., Ltd, Japan) via a feed line 1, into the distillation column 101 which was packed with a Metal Gauze CY packing (made by Sulzer Chemtech Ltd., Switzerland) and had a reboiler 111 and a condenser 121, whereby purification was carried out by distillation. Distillate containing a high concentration of water from an upper portion of the distillation column 101 was condensed by the condenser 121, and recovered from a recovery line 3. Purified 3-methyl-1-butanol was transported out via the transfer line 2 from a lower portion of the distillation column 101. An alkyltin alkoxide catalyst composition containing dioctyl-bis(3-methylbutyloxy)tin and 1,1,3,3-tetraoctyl-1,3-bis(3-methylbutyloxy)-distannoxane was obtained from a lower portion of the column reactor 102, and was supplied into a thin film evaporator 103 (made by Kobelco Eco-Solutions Co., Ltd., Japan) via a transfer line 5. 3-Methyl-1-butanol was evaporated off using the thin film evaporator 103, and returned into the column reactor 102 via a condenser 123, a transfer line 8 and the transfer line 4. The alkyltin alkoxide catalyst composition was transported from a lower portion of the thin film evaporator 103 via a transfer line 7, and was supplied into an autoclave 104, the flow rate of the dioctyl-bis(3-methylbutyloxy)tin and 1,1,3,3-tetraoctyl-1,3-bis(3-methylbutyloxy)-distannoxane active component being adjusted to approximately 6627 g/Hr. Carbon dioxide was supplied at 973 g/Hr into the autoclave via a transfer line 9, the pressure in the autoclave being maintained at 4 MPa-G. The temperature in the autoclave was set to 120° C., the residence time was adjusted to approximately 4 hours, and reaction was carried out between the carbon dioxide and the alkyltin alkoxide catalyst composition, thus obtaining a reaction liquid containing bis(3-methylbutyl)carbonate. The reaction liquid was transferred into a carbon dioxide removal tank 105 via a transfer line 10 and a regulating valve, and residual carbon dioxide was removed, the carbon dioxide being recovered from a transfer line 11. Then, the reaction liquid was transported via a transfer line 12 into a thin film evaporator 106 (made by Kobelco Eco-Solutions Co., Ltd., Japan) set to a temperature of approximately 150° C. and a pressure of approximately 0.5 kPa, being supplied in with the 1,1,3,3-tetraoctyl-1,3-bis(3-methylbutyloxy)-distannoxane flow rate adjusted to approximately 5887 g/Hr, and bis(3-methylbutyl)carbonate-containing distillate was obtained, while the evaporation residue was circulated back into the column reactor 102 via a transfer line 13 and the transfer line 4, the 1,1,3,3-tetraoctyl-1,3-bis(3-methylbutyloxy)-distannoxane flow rate being adjusted to approximately 5887 g/Hr. The bis(3-methylbutyl)carbonate-containing distillate was supplied via a condenser 126 and a transfer line 14 at 957 g/Hr into a distillation column 107 which was packed with a Metal Gauze CY packing (made by Sulzer Chemtech Ltd., Switzerland) and had a reboiler 117 and a condenser 127, and distillation purification was carried out, whereby 99 wt % bis(3-methylbutyl)carbonate was obtained from a recovery line 15 at 944 g/Hr. Upon analyzing alkyltin alkoxide catalyst composition from the transfer line 13 by $^{119}$Sn-, $^1$H-, and $^{13}$C-NMR, it was found that the alkyltin alkoxide catalyst composition contained 1,1,3,3-tetraoctyl-1,3-bis(3-methylbutyloxy)-distannoxane, but did not contain dioctyl-bis(3-methylbutyloxy)tin. Continuous operation as above was carried out for approximately 240 hours, and then the alkyltin alkoxide catalyst composition was withdrawn from a withdrawal line 16 at 23 g/Hr, while 1,1,3,3-tetraoctyl-1,3-bis(3-methylbutyloxy)-distannoxane produced in step 1 was supplied in from a feed line 17 at 23 g/Hr. Upon withdrawing approximately 120 g of liquid from the withdrawal line 16 and carrying out $^{119}$Sn-NMR analysis, it was found that the liquid contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

Step 3: Obtaining of Dialkyltin Dialkoxide from Thermally Decomposed Matter-Containing Alkyltin Alkoxide Catalyst Composition 500 g of the thermally decomposed matter-containing alkyltin alkoxide catalyst composition obtained in step 2 was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 99 wt % of trioctyl(3-methylbutyloxy)tin. Approximately 391 g of a high boiling component was obtained, and upon carrying out $^{119}$Sn-NMR analysis thereon, this was found to contain 1,1,3,3-tetraoctyl-1,3-bis(3-methylbutyloxy)distannoxane, with a plurality of NMR shifts originating from thermally decomposed matter also being seen in a range of from −240 to −605 ppm. The high boiling component was mixed with 838 g (4.15 mol) of the bis(3-methylbutyl)carbonate produced in step 2 in a flask under a nitrogen atmosphere, and reaction was carried out for 5 hours at 140° C. and normal pressure. Then, the reaction liquid was supplied at 300 g/Hr into a molecular distillation apparatus, and residual carbonate was separated off at a temperature of approximately 150° C. and a pressure of approximately 0.5 kPa, and approximately 450 g of liquid was obtained as a high boiling component. The high boiling component was supplied at 300 g/Hr into a molecular distillation apparatus, and separation by distillation was carried out at a temperature of approximately 240° C. and a pressure of approximately 0.02 kPa, whereby 359 g of a low boiling component was obtained. The low boiling component contained 97 wt % of dioctyl-bis(3-methylbutyloxy)tin. On the other hand, for the high boiling component, a plurality of NMR shifts originating from the high boiling deactivated component were seen in a range of from −240 to −605 ppm.

Example 10

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 99 wt % of trioctyl(3-methylbutyloxy)tin. Approximately 390 g of a high boiling component was obtained, and upon carrying out $^{119}$Sn-NMR analysis thereon, this was found to contain, 1,1,3,3-tetraoctyl-1,3-bis(3-methylbutyloxy)distannoxane, with a plurality of NMR shifts originating from the high boiling deactivated component also being seen in a range of from −240 to −605 ppm. The high boiling component was mixed with 1400 g (6.93 mol) of the bis(3-methylbutyl)carbonate produced in step 2 in a flask under a nitrogen atmosphere, and reaction was carried out for 10 hours at 120° C. and normal pressure. Then, the reaction liquid was supplied at 300 g/Hr into a molecular distillation apparatus, and residual carbonate was separated off at a temperature of approximately 140° C. and a pressure of approximately 0.5 kPa, and approximately 450 g of liquid was obtained as a high boiling component. The liquid was supplied at 300 g/Hr into a molecular distillation apparatus; and separation by distillation was carried out at a temperature of approximately 240° C. and a pressure of approximately 0.01 kPa, whereby 360 g of a low boiling component was obtained. The low boiling component contained 96 wt % of dioctyl-bis(3-methylbutyloxy)tin. On the other hand, for the high boiling component, a plurality of NMR shifts originating from the high boiling deactivated component were seen in a range of from −240 to −605 ppm.

Example 11

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 98 wt % of trioctyl(3-methylbutyloxy)tin. Approximately 391 g of a high boiling component was obtained, and upon carrying out $^{119}$Sn-NMR analysis thereon, this was found to contain 1,1,3,3-tetraoctyl-1,3-bis(3-methylbutyloxy)distannoxane, with a plurality of NMR shifts originating from the high boiling deactivated component also being seen in a range of from −240 to −605 ppm. The high boiling component was mixed with 838 g of the bis(3-methylbutyl)carbonate produced in step 2 of Example 10 in a flask under a nitrogen atmosphere, and the liquid mixture was subjected to reaction at 140° C. in a column reactor 201 as shown in FIG. 3. Heli-pak No. 3 (made by Tokyo Tokushu Kanaami, Japan) was packed into a SUS316 tube reactor of inside diameter 15 mm and total length 1635 mm (effective length 1450 mm) having a supply line 21 and a low boiling component recovery line 24 attached to an upper portion 221 of the reactor, and a supply line 22 and a recovery line 23 attached to a lower portion 211 of the reactor, and the tube reactor was heated using a heater set to 150° C. The liquid mixture was supplied in at 30 g/Hr via the supply line 21 using a liquid feeding pump, and nitrogen gas was supplied in at approximately 60 ml/min from the supply line 22. The residence time in the reactor was approximately 25 minutes. A low boiling point component containing carbon dioxide was withdrawn from the low boiling component recovery line 24 in a gaseous form, and a high boiling component began to flow out from the recovery line 23. Operation was continued in this state with continuous liquid feeding and continuous withdrawal, whereby approximately 1200 g of the high boiling component was recovered. Then, the high boiling component was supplied at 300 g/Hr into a molecular distillation apparatus, and residual carbonate was separated off at a temperature of approximately 140° C. and a pressure of approximately 0.4 kPa, and approximately 450 g of liquid was obtained as a high boiling component. The liquid was supplied at 300 g/Hr into a molecular distillation apparatus, and separation by distillation was carried out at a temperature of approximately 240° C. and a pressure of approximately 0.01 kPa, whereby 359 g of a low boiling component was obtained. The low boiling component contained 96 wt % of dioctyl-bis(3-methylbutyloxy)tin. On the other hand, for the high boiling component, a plurality of NMR shifts originating from the high boiling deactivated component were seen in a range of from −240 to −605 ppm.

Example 12

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 98 wt % of trioctyl(3-methylbutyloxy)tin. Approximately 391 g of a high boiling component was obtained, and upon carrying out $^{119}$Sn-NMR analysis thereon, this was found to contain 1,1,3,3-tetraoctyl-1,3-bis(3-methylbutyloxy)distannoxane, with a plurality of NMR shifts originating from the high boiling deactivated component also being seen in a range of from −240 to −605 ppm. The high boiling component was mixed with 420 g (2.08 mol) of the bis(3-methylbutyl)carbonate produced in step 2 of Example 10 in a flask under a nitrogen atmosphere, and reaction was carried out for 10 hours at 140° C. Then, the reaction liquid was supplied at 300 g/Hr into a molecular distillation apparatus, and residual carbonate was separated off at a temperature of approximately 140° C. and a pressure of approximately 0.5 kPa, and approximately 450 g of liquid was obtained as a high boiling component. The liquid was supplied at 300 g/Hr into a molecular distillation apparatus, and separation by distillation was carried out at a temperature of approximately 240° C. and a pressure of approximately 0.01 kPa, whereby 359 g of a low boiling component was obtained. The low boiling component contained 97 wt % of dioctyl-bis(3-methylbutyloxy)tin. On the other hand, for the high boiling component, a plurality of NMR shifts originating from the high boiling deactivated component were seen in a range of from −240 to −605 ppm.

Example 13

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 98 wt % of trioctyl(3-methylbutyloxy)tin. Approximately 391 g of a high boiling component was obtained, and upon carrying out $^{119}$Sn-NMR analysis thereon, this was found to contain 1,1,3,3-tetraoctyl-1,3-bis(3-methylbutyloxy)distannoxane, with a plurality of NMR shifts originating from the high boiling deactivated component also being seen in a range of from −240 to −605 ppm. The high boiling component was mixed with 420 g (2.08 mol) of the bis(3-methylbutyl)carbonate produced in step 2 of Example 10 in a flask under a nitrogen atmosphere, and reaction was carried out for 3 hours at 160° C. and normal pressure. Then, the reaction liquid was supplied at 300 g/Hr into a molecular distillation apparatus, and residual carbonate was separated off at a temperature of approximately 140° C. and a pressure of approximately 0.5 kPa, and approximately 450 g of liquid was obtained as a high boiling component. The liquid was supplied at 300 g/Hr into a molecular distillation apparatus, and separation by distillation was carried out at a temperature of approximately 240° C. and a pressure of approximately 0.01 kPa, whereby 361 g of a low boiling component was obtained. The low boiling component contained 96 wt % of dioctyl-bis(3-methylbutyloxy)tin. On the other hand, for the high boiling component, a plurality of NMR shifts originating from the high boiling deactivated component were seen in a range of from −240 to −605 ppm.

Example 14

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 98 wt % of trioctyl(3-methylbutyloxy)tin. Approximately 391 g of a high boiling component was obtained, and upon carrying out $^{119}$Sn-NMR analysis thereon, this was found to contain 1,1,3,3-tetraoctyl-1,3-bis(3-methylbutyloxy)distannoxane, a plurality of NMR shifts originating from thermally decomposed matter also being seen in a range of from −240 to −605 ppm. The high boiling component was mixed with 420 g (2.08 mol) of the bis(3-methylbutyl)carbonate produced in step 2 of Example 10 as a reactant, and reaction was carried out for 6 hours at 140° C. Then, the reaction liquid was supplied at 300 g/Hr into a molecular distillation apparatus, and residual carbonate was separated off at a temperature of approximately 140° C. and a pressure of approximately 0.5 kPa, and approximately 450 g of liquid was obtained as a high boiling component.

(Separating Out of Dialkyltin Dialkoxide by Distillation)

Next, using a gas-tight syringe (made by Hamilton), 400 g of the liquid was put into a 500 mL three-neck flask equipped with a three-way stopcock, a condenser, a distillate receiver and a thermometer, while passing in 0.3 L/min of nitrogen gas via the three-way stopcock. The flask was immersed in an oil bath heated to approximately 240° C. The pressure in the apparatus was gradually reduced, and distillation was carried out at approximately 0.02 kPa. 344 g of a low boiling component was obtained, this containing 96 wt % of dioctyl-bis(3-methylbutyloxy)tin according to the results of $^{119}$Sn-NMR analysis. The residual matter in the flask obtained contained approximately 1 wt % of 1,1,3,3-tetraoctyl-1,3-bis(3-methylbutyloxy)-distannoxane, and tin compounds exhibiting a plurality of chemical shifts in a range of from −240 to −605 ppm originating from the high boiling deactivated component.

Example 15

Step 1: Production of tetraalkyldialkoxydistannoxane 700 g (1.94 mol) of dioctyltin oxide (made by Sankyo Organic Chemicals Co., Ltd., Japan) and 1600 g (15.7 mol) of 2-ethyl-1-butanol (made by Chisso Corporation, Japan) were put into a 3000 mL flask. The flask containing the mixture, which was a white slurry, was attached to an evaporator (R-144, made by Sibata, Japan) having a temperature regulator-equipped oil bath (OBH-24, made by Masuda Corporation, Japan), a vacuum pump (G-50A, made by Ulvac, Japan) and a vacuum controller (VC-10S, made by Okano Works Ltd., Japan) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure. The oil bath temperature was set to 157° C., and the flask was immersed in the oil bath and rotation of the evaporator was commenced. With the purge valve of the evaporator left open, rotational agitation and heating were carried out for approximately 40 minutes at normal pressure, and then the purge valve was closed, and the pressure in the system was gradually reduced, and water-containing 2-ethyl-1-butanol was distilled off with the pressure in the system at from 84 to 65 kPa. This state was maintained for 7 hours, and then the pressure in the system was further reduced, and excess 2-ethyl-1-butanol was distilled off. Once the distillate stopped coming off, the flask was lifted out from the oil bath. The reaction liquid was a transparent liquid. After lifting the flask out from the oil bath, the purge valve was gradually opened, so as to return the pressure in the system to normal pressure. 883 g of reaction liquid was obtained in the flask. According to $^{119}$Sn-, $^{1}$H-, and $^{13}$C-NMR analysis results, the product 1,1,3,3-tetraoctyl-1,3-bis(2-ethylbutyloxy)-distannoxane was obtained at a yield of 99% based on the dioctyltin oxide. The same procedure was repeated twelve times, thus obtaining a total of 10600 g of 1,1,3,3-tetraoctyl-1,3-bis(2-ethylbutyloxy)-distannoxane.

Step 2: Production of Carbonate, Obtaining Thermally Decomposed Matter-Containing Alkyltin Alkoxide Catalyst Composition A carbonate was produced using a continuous production apparatus as shown in FIG. 2. The 1,1,3,3-tetraoctyl-1,3-bis(2-ethylbutyloxy)-distannoxane produced in step 1 was supplied at 6074 g/Hr from a supply line 4 into a column reactor 102 of inside diameter 151 mm and effective length 5040 mm packed with a Metal Gauze CY packing (made by Sulzer Chemtech Ltd., Switzerland), and 2-ethyl-1-butanol (made by Chisso Corporation, Japan) that had been purified in a distillation column 101 was supplied at 12260 g/Hr from a supply line 2 into the column reactor 102. The liquid temperature in the reactor was adjusted to 160° C. using a heater and a reboiler 112, and the pressure was adjusted to approximately 31 kPa-G using a pressure regulating valve. The residence time in the reactor was approximately 17 minutes. 12260 g/Hr of water-containing 2-ethyl-1-butanol was transported from an upper portion of the reactor via a transfer line 6, and 958 g/Hr of 2-ethyl-1-butanol (made by Chisso Corporation, Japan) via a supply line 1, into the distillation column 101 which was packed with a Metal Gauze CY packing (made by Sulzer Chemtech Ltd., Switzerland) and had a reboiler 111 and a condenser 121, whereby purification was carried out by distillation. Distillate containing a high concentration of water from an upper portion of the distillation column 101 was condensed by the condenser 121, and recovered from a recovery line 3. Purified 2-ethyl-1-butanol was transported out via the transfer line 2 from a lower portion of the distillation column 101. An alkyltin alkoxide catalyst composition containing dioctyl-bis(2-ethylbutyloxy)tin and 1,1,3,3-tetraoctyl-1,3-bis(2-ethylbutyloxy)-distannoxane was obtained from a lower portion of the column reactor 102, and was supplied into a thin film evaporator 103 (made by Kobelco Eco-Solutions Co., Ltd., Japan) via a transfer line 5. 2-ethyl-1-butanol was evaporated off using the thin film evaporator 103, and returned into the column reactor 102 via a condenser 123, a transfer line 8 and the transfer line 4. The alkyltin alkoxide catalyst composition Was transported from a lower portion of the thin film evaporator 103 via a transfer line 7, and was supplied into an autoclave 104, the flow rate of the dioctyl-bis(2-ethylbutyloxy)tin and 1,1,3,3-tetraoctyl-1,3-bis(2-ethylbutyloxy)-distannoxane active component being adjusted to approximately 6945 g/Hr. Carbon dioxide was supplied at 973 g/Hr into the autoclave via a transfer line 9, the pressure in the autoclave being maintained at 4 MPa-G. The temperature in the autoclave was set to 120° C., the residence time was adjusted to approximately 4 hours, and reaction was carried out between the carbon dioxide and the alkyltin alkoxide catalyst composition, thus obtaining a reaction liquid containing bis(2-ethylbutyl)carbonate. The reaction liquid was transferred into a carbon dioxide removal tank 105 via a transfer line 10 and a regulating valve, and residual carbon dioxide was removed, the carbon dioxide being recovered from a transfer line 11. Then, the reaction liquid was transported via a transfer line 12 into a thin film evaporator 106 (made by Kobelco Eco-Solutions Co., Ltd., Japan) set to a temperature of approximately 150° C. and a pressure of approximately 0.3 kPa, being supplied in with the 1,1,3,3-tetraoctyl-1,3-bis(2-ethylbutyloxy)-distannoxane flow rate adjusted to approximately 6074 g/Hr, and bis(2-ethylbutyl) carbonate-containing distillate was obtained, while the evaporation residue was circulated back into the column reactor 102 via a transfer line 13 and the transfer line 4, the 1,1,3,3-tetraoctyl-1,3-bis(2-ethylbutyloxy)-distannoxane flow rate being adjusted to approximately 6074 g/Hr. The bis(2-ethylbutyl)carbonate-containing distillate was supplied via a condenser 126 and a transfer line 14 at 1090 g/Hr into a distillation column 107 which was packed with a Metal Gauze CY packing (made by Sulzer Chemtech Ltd., Switzerland) and had a reboiler 117 and a condenser 127, and distillation purification was carried out, whereby 99 wt % bis(2-ethylbutyl)carbonate was obtained from a recovery line 15 at 1075 g/Hr. Upon analyzing alkyltin alkoxide catalyst composition from the transfer line 13 by $^{119}$Sn-, $^{1}$H-, and $^{13}$C-NMR, it was found that the alkyltin alkoxide catalyst composition contained 1,1,3,3-tetraoctyl-1,3-bis(2-ethylbutyloxy)-distannoxane, but did not contain dioctyl-bis(2-ethylbutyloxy) tin. Continuous operation as above was carried out for approximately 160 hours, and then the alkyltin alkoxide catalyst composition was withdrawn from a withdrawal line 16 at 30 g/Hr, while 1,1,3,3-tetraoctyl-1,3-bis(2-ethylbutyloxy)-distannoxane produced in step 1 was supplied in from a feed line 17 at 30 g/Hr. Upon withdrawing approximately 120 g of liquid from the withdrawal line 16 and carrying out $^{119}$Sn-NMR analysis, it was found that the liquid contained approximately 60 wt % of 1,1,3,3-tetraoctyl-1,3-bis(2-ethylbutyloxy)-distannoxane, and in addition to this there was trioctyl (2-ethylbutyloxy)tin and a plurality of NMR shifts for a high boiling deactivated component originating from thermal decomposition were seen in a range of from −240 to −605 ppm.

(Obtaining of Dialkyltin Dialkoxide from Thermally Decomposed Matter-Containing Alkyltin Alkoxide Catalyst Composition)

100 g of the above thermally decomposed matter-containing alkyltin alkoxide catalyst composition was supplied at 5 g/min into a molecular distillation apparatus (MS-300, made by Sibata Scientific Technology Ltd., Japan), and a volatile component was removed at a temperature of approximately 240° C. and a pressure of approximately 0.02 kPa. This low boiling component contained 99 wt % of trioctyl(2-ethylbutyloxy)tin. Approximately 77 g of a high boiling component was obtained, and upon carrying out $^{119}$Sn-NMR analysis thereon, this was found to contain 1,1,3,3-tetraoctyl-1,3-bis (2-ethylbutyloxy)distannoxane, with a plurality of NMR shifts originating from the high boiling deactivated component also being seen in a range of from −240 to −605 ppm. The high boiling component was mixed with 182 g (0.79 mol) of the bis(2-ethylbutyl)carbonate produced in step 2, and reaction was carried out for 6 hours at 140° C. and normal pressure. Then, the reaction liquid was supplied at 5 g/min into a molecular distillation apparatus, and residual carbonate was separated off at a temperature of approximately 150° C. and a pressure of approximately 0.3 kPa, and approximately 88 g of liquid was obtained as a high boiling component. The liquid was supplied at 5 g/min into a molecular distillation apparatus, and separation by distillation was carried out at a temperature of approximately 250° C. and a pressure of approximately 0.01 kPa, whereby 71 g of a low boiling component was obtained. The low boiling component contained 97 wt % of dioctyl-bis(2-ethylbutyloxy)tin. On the other hand, for the high boiling component, a plurality of NMR shifts originating from the high boiling deactivated component were seen in a range of from −240 to −605 ppm.

Example 16

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 1. The $^{119}$Sn-NMR analysis results were that the thermally decomposed matter-containing alkyltin alkoxide catalyst composition contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 185° C. and a pressure of approximately 0.06 kPa. This low boiling component contained 98 wt % of tributyl(3-methylbutyloxy)tin. Approximately 390 g of a high boiling component was obtained, and upon carrying out $^{119}$Sn-NMR analysis thereon, this was found to contain 1,1,3,3-tetrabutyl-1,3-bis(3-methylbutyloxy)distannoxane, with a plurality of NMR shifts originating from the high boiling deactivated component also being seen in a range of from −240 to −605 ppm. 100 g of the high boiling component was mixed with 25 g (0.1 mol) of dibutyltin oxide (made by Sankyo Organic Chemicals Co., Ltd., Japan) and 560 g (0.089 mol) of the bis(3-methylbutyl)carbonate produced in step 2 of Example 1 in a 1000 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to approximately 150° C., and the flask was immersed in the oil bath and rotation of the evaporator was commenced. With the purge valve of the evaporator left open, rotational agitation, was carried out for approximately 4 hours at normal pressure, and then the purge valve was closed, and the pressure in the system was gradually reduced, and excess bis(3-methylbutyl)carbonate was removed with the pressure in the system at from 50 to 1 kPa, and then once distillate stopped coming off, the flask was lifted out from the oil bath. Approximately 168 g of reaction liquid was obtained. The reaction liquid was supplied at 5 g/min into a molecular distillation apparatus, and separation by distillation was carried out at a temperature of approximately 185° C. and a pressure of approximately 0.01 kPa, whereupon 144 g of a low boiling component was obtained. The low boiling component contained 98 wt % of dibutyl-bis (3-methylbutyloxy)tin. On the other hand, for the high boiling component, a plurality of NMR shifts originating from the high boiling deactivated component were seen in a range of from −240 to −605 ppm.

Example 17

Approximately 100 g of dioctyltin-bis(3-methylbutyloxy) tin obtained from Example 10 was put into a 200 ml autoclave (made by Toyo Koatsu Co., Ltd., Japan), and the temperature was increased to 120° C. Then, carbon dioxide was introduced into the autoclave, and the pressure was adjusted to 4 MPa. The dioctyltin-bis(3-methylbutyloxy)tin and carbon dioxide were reacted together for 4 hours, and then the reaction liquid was recovered. The reaction liquid was analyzed, and was found to contain approximately 19 wt % of bis(3-methylbutyl)carbonate.

Example 18

A thermally decomposed matter-containing alkyltin alkoxide catalyst composition was obtained through the same process as in steps 1 and 2 of Example 1. The $^{119}$Sn-NMR analysis results were that the thermally decomposed matter-containing alkyltin alkoxide catalyst composition contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts originating from a high boiling deactivated component were seen in a range of from −240 to −605 ppm. 500 g of the thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of 155° C. and a pressure of approximately 0.06 kPa. This low boiling component contained 98 wt % of tributyl(3-methylbutyloxy)tin. Approximately 386 g of a high boiling component was obtained, and upon carrying out $^{119}$Sn-NMR analysis thereon, this was found to contain the active component 1,1,3,3-tetrabutyl-1,3-bis(3-methylbutyloxy)distannoxane, with a plurality of NMR shifts originating from the high boiling deactivated component also being seen in a range of from −240 to −605 ppm. 50 g of the alkyltin alkoxide catalyst composition containing the active component and the high boiling deactivated component was transferred into a 100 mL flask, and a condenser, a distillate receiver and a thermometer were attached so that reduced pressure distillation could be carried out using the flask. The flask was immersed in an oil bath heated to 258° C., and was thus heated at normal pressure. Upon heating for approximately 30 minutes, the temperature of the contents of the flask reached 250° C., but distillate could not be recovered. The pressure in the system was gradually reduced, reaching approximately 0.01 kPa, but distillate could still not be recovered.

Comparative Example 1

Production of Carbonate, Obtaining Thermally Decomposed Matter-Containing Alkyltin Alkoxide Catalyst Composition A thermally decomposed matter-containing alkyltin alkoxide catalyst composition was obtained through the same process as in steps 1 and 2 of Example 1. The $^{119}$Sn-NMR analysis results were that the thermally decomposed matter-containing alkyltin alkoxide catalyst composition contained approximately 60 wt % of 1,1,3,3-tetrabutyl-1,3-bis(3-methylbutyloxy)-distannoxane, and in addition to this there was tributyl(3-methylbutyloxy)tin and a plurality of NMR shifts originating from a high boiling deactivated component were seen in a range of from −240 to −605 ppm.

(Separation and Recovery of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of 155° C. and a pressure of 0.13 kPa. This low boiling component contained 99 wt % of tributyl(3-methylbutyloxy)tin. Approximately 386 g of a high boiling component was obtained as a liquid, and upon carrying out $^{119}$Sn-NMR analysis thereon, this was found to contain 1,1,3,3-tetrabutyl-1,3-bis(3-methylbutyloxy)distannoxane, with a plurality of NMR shifts originating from the high boiling deactivated component also being seen in a range of from −240 to −605 ppm. 50 g of the liquid containing the 1,1,3,3-tetrabutyl-1,3-bis(3-methylbutyloxy)distannoxane and the high boiling deactivated component was taken, and cooled to 0° C., and then upon leaving for 60 Hr, solid precipitated out. The solid was separated off from the liquid by filtering under a nitrogen atmosphere. Approximately 10 g of the solid was recovered, and upon carrying out $^{119}$Sn-NMR analysis, it was found that the solid contained approximately 20 wt % of 1,1,3,3-tetrabutyl-1,3-bis(3-methylbutyloxy)distannoxane, and in addition to this a plurality of NMR shifts originating from the high boiling deactivated component were seen in a range of from −240 to −605 ppm. $^{119}$Sn-NMR analysis was also carried out on the filtrate, whereupon it was found that the filtrate contained approximately 75 wt % of 1,1,3,3-tetrabutyl-1,3-bis(3-methylbutyloxy)distannoxane, with a plurality of NMR shifts originating from the high boiling deactivated component also being seen in a range of from −240 to −605 ppm.

Comparative Example 2

Production of Carbonate, Obtaining Thermally Decomposed Matter-Containing Alkyltin Alkoxide Catalyst Composition A thermally decomposed matter-containing alkyltin alkoxide catalyst composition was obtained through the same process as in steps 1 and 2 of Example 7. The $^{119}$Sn-NMR analysis results were that the thermally decomposed matter-containing alkyltin alkoxide catalyst composition contained approximately 70 wt % of 1,1,3,3-tetrabutyl-1,3-di(butyloxy)-distannoxane, and in addition to this there was tributyltin butoxide and a plurality of NMR shifts originating from a high boiling deactivated component were seen in a range of from −240 to −605 ppm.

(Separation and Recovery of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of 155° C. and a pressure of 0.13 kPa. This low boiling component contained 98 wt % of tributyltin butoxide. Approximately 386 g of a high boiling component was obtained as a liquid, and upon carrying out $^{119}$Sn-NMR analysis thereon, this was found to contain 1,1,3,3-tetrabutyl-1,3-di(butyloxy)distannoxane, with a plurality of NMR shifts originating from the high boiling deactivated component also being seen in a range of from −240 to −605 ppm. 50 g of the liquid containing the 1,1,3,3-tetrabutyl-1,3-di(butyloxy)distannoxane and the high boiling deactivated component was taken, and cooled to 0° C., and then upon leaving for 120 Hr, solid precipitated out. The solid was separated off from the liquid by filtering under a nitrogen atmosphere. Approximately 5 g of the solid was recovered, and upon carrying out $^{119}$Sn-NMR analysis, it was found that the solid contained approximately 22 wt % of 1,1,3,3-tetrabutyl-1,3-di(butyloxy)distannoxane, and in addition to this a plurality of NMR shifts originating from the high boiling deactivated component were seen in a range of from −240 to −605 ppm. $^{119}$Sn-NMR analysis was also carried out on the filtrate, whereupon it was found that the filtrate contained approximately 70 wt % of 1,1,3,3-tetrabutyl-1,3-di(butyloxy)distannoxane, with a plurality of NMR shifts originating from the high boiling deactivated component also being seen in a range of from −240 to −605 ppm.

Comparative Example 3

Approximately 100 g of the high boiling deactivated component obtained from Example 10 was put into a 200 ml autoclave (made by Toyo Koatsu Co., Ltd., Japan), and the temperature was increased to 120° C. Then, carbon dioxide was introduced into the autoclave, and the pressure was adjusted to 4 MPa. The high boiling deactivated component and carbon dioxide were reacted together for 4 hours, and then the reaction liquid was recovered. The reaction liquid was analyzed, and was found to contain approximately 0.3 wt % of bis(3-methylbutyl)carbonate.

Comparative Example 4

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 98 wt % of trioctyl(3-methylbutyloxy)tin. Approximately 390 g of a high boiling component was obtained, and upon carrying out $^{119}$Sn-NMR analysis thereon, this was found to contain 1,1,3,3-tetraoctyl-1,3-bis(3-methylbutyloxy)distannoxane, with a plurality of NMR shifts originating from the high boiling deactivated component also being seen in a range of from −240 to −605 ppm. 100 g of the high boiling component and 1770 g (17.7 mol) of cyclohexanol (made by Aldrich) were mixed together in a 3000 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works. Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to 170° C., and the flask was immersed in the oil bath and rotation of the evaporator was commenced. With the purge valve of the evaporator left open, rotational agitation was carried out for approximately 1 hour at normal pressure, and then the purge valve was closed, and the pressure in the system was gradually reduced, and a dehydration reaction was carried out for approximately 6 hours while distilling off water-containing cyclohexanol with the pressure in the system at from 80 to 30 kPa. Then, excess cyclohexanol was distilled off, and then once distillate stopped coming off, the flask was lifted out from the oil bath. Approximately 120 g of reaction liquid was obtained. The reaction liquid was supplied at 3 g/min into a molecular distillation apparatus, and separation by distillation was carried out at a temperature of approximately 240° C. and a pressure of approximately 0.01 kPa, whereupon 40 g of a low boiling component was obtained. The low boiling component contained 95 wt % of dioctyl-bis(cyclohexyloxy)tin. On the other hand, the high boiling component contained approximately 50 wt % of the active component 1,1,3,3-tetraoctyl-1,3-bis(cyclohexyloxy)-distannoxane, with a plurality of NMR shifts originating from the high boiling deactivated component also being seen in a range of from −240 to −605 ppm.

Comparative Example 5

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 98 wt % of trioctyl(3-methylbutyloxy)tin. Approximately 390 g of a high boiling component was obtained, and upon carrying out $^{119}$Sn-NMR analysis thereon, this was found to contain 1,1,3,3-tetraoctyl-1,3-bis(3-methylbutyloxy)distannoxane, with a plurality of NMR shifts originating from the high boiling deactivated component also being seen in a range of from −240 to −605 ppm. 100 g of the high boiling component and 639 g (7.1 mol) of dimethyl carbonate (made by Aldrich) were mixed together in a 1000 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to approximately 105° C., and the flask was immersed in the oil bath and rotation of the evaporator was commenced. With the purge valve of the evaporator left open, rotational agitation was carried out for approximately 5 hours at normal pressure, and then the purge valve was closed, and the pressure in the system was gradually reduced, and excess dimethyl carbonate was distilled off with the pressure in the system at from 80 to 30 kPa, and then once distillate stopped coming off, the flask was lifted out from the oil bath. Approximately 120 g of reaction liquid was obtained. The reaction liquid was supplied at 3 g/min into a molecular distillation apparatus, and separation by distillation was carried out at a temperature of approximately 210° C. and a pressure of approximately 0.02 kPa, whereupon 16 g of a low boiling component was obtained. The low boiling component contained 96 wt % of dioctyltin dimethoxide. On the other hand, the high boiling component contained approximately 65 wt % of a mixture of the active components 1,1,3,3-tetraoctyl-1,3-bis(3-methylbutyloxy)-distannoxane and 1,1,3,3-tetraoctyl-1,3-dimethoxy-distannoxane, with a plurality of NMR shifts originating from the high boiling deactivated component also being seen in a range of from −240 to −605 ppm.

Comparative Example 6

Obtaining of Thermally Decomposed Matter-Containing Alkyltin Alkoxide Catalyst Composition from Carbonate Production A thermally decomposed matter-containing alkyltin alkoxide catalyst composition was obtained through the same process as in steps 1 and 2 of Example 9. The $^{119}$Sn-NMR analysis results were that the thermally decomposed matter-containing alkyltin alkoxide catalyst composition contained approximately 60 wt % of 1,1,3,3-tetraoctyl-1,3-bis(3-methylbutyloxy)-distannoxane, and in addition to this there was trioctyl(3-methylbutyloxy)tin and a plurality of NMR shifts originating from a high boiling deactivated component were seen in a range of from −240 to −605 ppm.

(Obtaining of Dialkyltin Dialkoxide from Thermally Decomposed Matter-Containing Alkyltin Alkoxide Catalyst Composition)

500 g of the above thermally decomposed matter-containing alkyltin alkoxide catalyst composition was supplied at 300 g/Hr into a molecular distillation apparatus (MS-300, made by Sibata Scientific Technology Ltd., Japan), and a volatile component was removed at a temperature of approximately 230° C. and a pressure of approximately 0.02 kPa. This low boiling component contained 98 wt % of trioctyl(3-methylbutyloxy)tin. Approximately 390 g of a high boiling component was obtained, and upon carrying out $^{119}$Sn-NMR analysis thereon, this was found to contain 1,1,3,3-tetraoctyl-1,3-bis(3-methylbutyloxy)distannoxane, with a plurality of NMR shifts originating from the high boiling deactivated component also being seen in a range of from −240 to −605 ppm. 100 g of the high boiling component and 18 g (0.089 mol) of the bis(3-methylbutyl)carbonate produced in step 2 of Example 10 were mixed together in a 500 mL flask in a glove box purged with nitrogen, and the flask was stoppered. The flask containing the mixture was attached to an evaporator (R-144, made by Sibata) having a temperature regulator-equipped oil bath (OBH-24, made by Masuda Corporation), a vacuum pump (G-50A, made by Ulvac) and a vacuum controller (VC-10S, made by Okano Works Ltd.) connected thereto. The outlet of a purge valve of the evaporator was connected to a line for nitrogen gas flowing at normal pressure. The purge valve of the evaporator was closed, and the pressure in the system was reduced, and then the purge valve was gradually opened, so as to pass nitrogen into the system, and thus return the system to normal pressure, whereby the reaction apparatus was purged with nitrogen. The oil bath temperature was set to approximately 140° C., and the flask was immersed in the oil bath and rotation of the evaporator was commenced. With the purge valve of the evaporator left open, rotational agitation was carried out for approximately 3 hours at normal pressure, and then the purge valve was closed, and the pressure in the system was gradually reduced, and unreacted bis(3-methylbutyl)carbonate was removed with the pressure in the system at from 50 to 1 kPa, and then once distillate stopped coming off, the flask was lifted out from the oil bath. Approximately 117 g of reaction liquid was obtained. The reaction liquid was supplied at 3 g/min into a molecular distillation apparatus, and separation by distillation was carried out at a temperature of approximately 240° C. and a pressure of approximately 0.01 kPa, whereupon 50 g of a low boiling component was obtained. The low boiling component contained 97 wt % of dioctyl-bis(3-methylbutyloxy)tin. On the other hand, the high boiling component contained approximately 25 wt % of the active component 1,1,3,3-tetraoctyl-1,3-bis(3-methylbutyloxy)-distannoxane, with a plurality of NMR shifts originating from the high boiling deactivated component also being seen in a range of from −240 to −605 ppm.

INDUSTRIAL APPLICABILITY

According to the present invention, a dialkyltin dialkoxide which is a useful component can be efficiently separated out and recovered from the undistillable alkyltin alkoxide catalyst composition containing the high boiling deactivated component and the active component, and hence the present invention is highly useful for industrial application.

We claim:
1. A method for separating out and recovering an active component, by converting the active component into a dialkyltin dialkoxide, from an undistillable alkyltin alkoxide catalyst composition for use in a carbonate production, which contains a high boiling deactivated component and the active component, the method comprising the steps of:
(1) reacting the alkyltin alkoxide catalyst composition with an alcohol and/or a carbonate, so as to obtain a reaction solution containing a product originating from the active component; and
(2) subjecting the reaction solution obtained in step (1) to distillation, so as to separate out and recover the dialkyltin dialkoxide from the product originating from the active component.

2. The separation recovery method according to claim 1, wherein the active component is a component having two tin-carbon bonds on each tin atom constituting an alkyltin alkoxide.

3. The separation recovery method according to claim 1, wherein the high boiling deactivated component has a boiling point higher than 250° C. at normal pressure.

4. The separation recovery method according to claim 1, wherein the alkyltin alkoxide catalyst composition is not capable of being separated by distillation into the high boiling deactivated component and the active component at not more than 250° C. at normal pressure.

5. The separation recovery method according to claim 1, wherein the active component is a tetraalkyldialkoxydistannoxane.

6. The separation recovery method according to claim 5, wherein the tetraalkyldialkoxydistannoxane is an alkyltin compound represented by following formula (1):

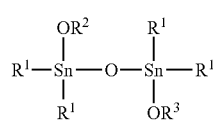

(1)

wherein $R^1$ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted or substituted aryl group having from 6 to 20 carbon atoms containing an alkyl selected from the group consisting of straight chain or branched alkyls having from 1 to 14 carbon atoms and cycloalkyls having from 5 to 14 carbon atoms; and each of $R^2$ and $R^3$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms.

7. The separation recovery method according to claim 1, wherein the high boiling deactivated component is an alkyltin compound containing tin atoms that in $^{119}$Sn-NMR analysis exhibit chemical shifts in a range of from −220 to −610 ppm based on tetramethyltin.

8. The separation recovery method according to claim 1, wherein the alcohol is represented by following formula (2):

(2)

wherein $R^4$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms.

9. The separation recovery method according to claim 1, wherein the carbonate is represented by following formula (3):

(3)

wherein each of $R^5$ and $R^6$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms.

10. The separation recovery method according to claim 1, wherein the dialkyltin dialkoxide is represented by following formula (4):

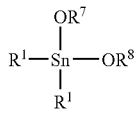

(4)

wherein R¹ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted or substituted aryl group having from 6 to 20 carbon atoms containing an alkyl selected from the group consisting of straight chain or branched alkyls having from 1 to 14 carbon atoms and cycloalkyls having from 5 to 14 carbon atoms; and each of $R^7$ and $R^8$ represents a straight chain or branched aliphatic group having from 1 to 12 carbon atoms, an alicyclic aliphatic group having from 5 to 12 carbon atoms, an unsubstituted or substituted aryl group having from 6 to 19 carbon atoms, or an aralkyl group having from 7 to 20 carbon atoms containing an alkyl selected from the group consisting of straight chain or branched alkyls having from 1 to 14 carbon atoms and cycloalkyls having from 5 to 14 carbon atoms; and each of $R^7$ and $R^8$ corresponds to an alkoxy group of the active component, $R^4$ in the alcohol, or $R^5$ or $R^6$ in the carbonate, wherein at least one of $R^7$ and $R^8$ corresponds to $R^4$, $R^5$ or $R^6$.

11. The separation recovery method according to claim 1, wherein the alkyltin alkoxide catalyst composition contains a dialkyltin oxide represented by following formula (5):

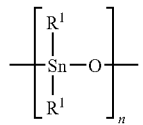

(5)

wherein R¹ represents a straight chain or branched alkyl group having from 1 to 12 carbon atoms, a cycloalkyl group having from 5 to 12 carbon atoms, a straight chain or branched alkenyl group having from 2 to 12 carbon atoms, an unsubstituted or substituted aryl group having from 6 to 19 carbon atoms, an aralkyl group having from 7 to 20 carbon atoms containing an alkyl selected from the group consisting of straight chain or branched alkyls having from 1 to 14 carbon atoms and cycloalkyls having from 5 to 14 carbon atoms, or an unsubstituted substituted aryl group having from 6 to 20 carbon atoms containing an alkyl selected from the group consisting of straight chain or branched alkyls having from 1 to 14 carbon atoms and cycloalkyls having from 5 to 14 carbon atoms.

12. The separation recovery method to claim 6, wherein each alkyl group of the tetraalkyldialkoxydistannoxane is an n-butyl group or an n-octyl group.

13. The separation recovery method according to claim 8, wherein the alcohol is an alcohol selected from aliphatic alkyl alcohols having from 4 to 8 carbon atoms.

14. The separation recovery method according to claim 9, wherein the carbonate is a carbonate in which at least one of $R^5$ and $R^6$ is selected from aliphatic alkyl groups having from 4 to 8 carbon atoms.

15. The separation recovery method according to claim 11, wherein the dialkyltin oxide is a dialkyltin oxide selected from di-n-butyl-tin oxide and di-n-octyl-tin oxide.

16. The separation recovery method according to claim 1, wherein in step (1), a ratio of a total number of mols of the alcohol and/or the carbonate to the number of mols of tin atoms contained in the active component is in a range of from 2 to 100.

17. The separation recovery method according to claim 1, wherein in step (1), a reaction temperature is in a range of from 60 to 180° C.

18. The separation recovery method according to claim 1, wherein the reaction of step (1) is carried out in a reactor of a type selected from the group consisting of a stirring tank reactor, a multi-stage stirring tank reactor, a packed column, a distillation column, a multi-stage distillation column, a continuous multi-stage distillation column, a reactor having a support therein, and a forced circulation reactor.

19. The separation recovery method according to claim 1, wherein in step (2), the separation by distillation is carried out in a distillation apparatus of a type selected from the group consisting of a multi-stage distillation column, a continuous multi-stage distillation column, a packed column, and a thin film evaporator.

20. A process for producing a carbonate using a dialkyltin dialkoxide separated out and recovered using the method according to claim 1.

* * * * *